(12) United States Patent
Nielsen et al.

(10) Patent No.: US 6,548,651 B1
(45) Date of Patent: Apr. 15, 2003

(54) MODIFIED PEPTIDE NUCLEIC ACID (PNA) MOLECULES

(75) Inventors: Peter E. Nielsen, Hjortevaenget 509, DK 2980 Kokkedal (DK); Liam Good, Stockholm (DK); Henrik Frydenlund Hansen, Rodovre (DK); Frederik Beck, Frederiksberg (DK); Leila Malik, Copenhagen (DK); Carsten Schou, Holte (DK); Margit Wissenbach, Copenhagen (DK); Birgit Kjaeldgaard Giwercman, Charlottenlund (DK)

(73) Assignees: Pantheco A/S (DK); Peter E. Nielsen (DK)

(*) Notice: Subject to any disclaimer, the term of this patent is extended or adjusted under 35 U.S.C. 154(b) by 23 days.

(21) Appl. No.: 09/689,155

(22) Filed: Oct. 12, 2000

Related U.S. Application Data

(60) Provisional application No. 60/211,758, filed on Jun. 14, 2000, provisional application No. 60/211,878, filed on Jun. 14, 2000, provisional application No. 60/211,435, filed on Jun. 14, 2000, provisional application No. 60/159,679, filed on Oct. 15, 1999, and provisional application No. 60/159,684, filed on Oct. 15, 1999.

(30) Foreign Application Priority Data

| Oct. 13, 1999 | (DK) | PA 1999 01471 |
|---|---|---|
| Oct. 13, 1999 | (DK) | PA 1999 01467 |
| Dec. 3, 1999 | (DK) | PA 1999 01734 |
| Dec. 3, 1999 | (DK) | PA 1999 01735 |
| Mar. 28, 2000 | (DK) | PA 2000 00522 |
| Apr. 19, 2000 | (DK) | PA 2000 00670 |
| Apr. 19, 2000 | (DK) | PA 2000 00671 |

(51) Int. Cl.$^7$ ............... C07H 21/04; C07K 38/00; C07K 7/00
(52) U.S. Cl. ............... 536/23.1; 536/23.7; 536/24.32; 530/300; 530/328
(58) Field of Search ............... 536/23.1, 23.7, 536/24.32; 530/328, 300

(56) References Cited

U.S. PATENT DOCUMENTS

| 5,652,211 A | 7/1997 | Porro ............... 514/11 |
| 5,777,078 A | 7/1998 | Bayley et al. ............... 530/350 |
| 5,834,430 A | * 11/1998 | Porro et al. |

FOREIGN PATENT DOCUMENTS

| DK | PA 1999 01467 | 10/1999 |
| DK | PA 1999 01471 | 10/1999 |
| DK | PA 1999 01734 | 12/1999 |
| DK | PA 1999 01735 | 12/1999 |
| DK | PA 2000 00522 | 3/2000 |
| DK | PA 2000 00670 | 4/2000 |
| DK | PA 2000 00671 | 4/2000 |

(List continued on next page.)

OTHER PUBLICATIONS

Dufourcq, J. et al., "Molecular assembling of DNA with amphipathic peptides", *FEBS Lett.*, 1998, vol. 421, No. 1, pp. 7–11.

Ishihara, T. et al., "Rules for Stand Invasion by Chemically Modified Oligonucleotides", *J. Am. Chem. Soc.*, 1999, vol. 121, No. 10, pp. 2012–2020.

(List continued on next page.)

*Primary Examiner*—W. Gary Jones
*Assistant Examiner*—B J Forman
(74) *Attorney, Agent, or Firm*—Woodcock Washburn LLP

(57) ABSTRACT

The present invention relates to novel drugs which may be used in combating infectious micro-organisms, particularly bacteria. More specifically, the invention relates to peptide nucleic acid (PNA) sequences that are modified by conjugating cationic peptides to the PNA moiety in order to obtain novel PNA molecules that exhibit enhanced anti-infective properties.

1 Claim, 7 Drawing Sheets

DNA

PNA

FOREIGN PATENT DOCUMENTS

| WO | WO 92/2072 | 11/1992 |
|---|---|---|
| WO | WO 92/20703 | 11/1992 |
| WO | 96/02558 | 2/1996 |
| WO | WO 96/11205 | 4/1996 |
| WO | 96/38163 | 12/1996 |
| WO | WO 98/03533 | 1/1998 |
| WO | WO 98/32467 | 7/1998 |
| WO | WO 98/52614 | 11/1998 |
| WO | WO 99/05302 | 2/1999 |
| WO | WO 99/13893 | 3/1999 |
| WO | WO 99/14226 | 3/1999 |

OTHER PUBLICATIONS

Simmons, C. G. et al., "Synthesis and membrane permeability of pna–peptide conjugates", *Bioorganics & Medicinal Chemistry Letters*, Dec. 2, 1997, vol. 7, No. 23, pp. 3001–3006.

Arthur, M., et al., "Glycopeptide resistance in enterocci," *Trends Microbiol*, 1996, 4(10), 401–407.

Baquero, F., "Pneumococcal resistance to β–lactam antibiotics: a global geographic overview," *Microb Drug Reist.*, 1995, 1(2), 115–120.

Berge, S.M., et al., "Pharmaceutical salts," *J. Pharm. Sciences*, 1977, 66(1), 1–19.

Bert, F., et al., "Comparitve distribution of resistance patterns and serotypes in *pseudomonas aeruginosa* isolates from intensive care units and other wards," *J. Antimicrob Chemother*, 1996, 37, 809.

Broome–Smith, et al., "The nucleotide sequences of the ponA and ponB genes encoding penicillin–binding proteins 1A and 1B of *Escherichia coli* K12," *FEBS*, 1985, 147, 437–446.

Carmelli, Y., et al., "The association between antecedent vancomycin treatment and hospital–acquired vancomycin–resistant enterococci," *Arch Intern. Med.*, 1999, 159, 2461–2468.

Chambers, H.F., "Methicillin resistance in staphylococci: Molecular and biochemical basis and clinical implications," *Clin. Microbiol. Rev.*, 1997, 10(4), 781–791.

CDR Weekly, *Communicable Disease Report*, ISSN 1350–9357, Feb. 19, 1999, 9(8), 65–75.

CDR Review, *Communicable Disease Report*, ISSN 1350–9349, Nov. 10, 1999, 5(7), R173–R188.

Cookson, B.D., "Nosocomial antimicrobial resistance surveillance," *J. Hosp. Infec.*, 1999, 43 (Supplement), S97–S103.

Costerton, J.W., et al., "Bacterial biofilms in nature and disease," *Ann Rev. Microbiol.*, 1987, 41, 435–464.

Davis, J., et al., "Inactivation of antibiotics and the dissemination of resistance genes," *Science*, 1994, 264, 375–382.

Demidov, et al., "Stability of peptide nucleic acids in human serum and cellular extracts," *P.E. Biochem. Pharmacol.*, 1994, 48(6), 1310–1313.

Egholm, M., et al., "PNA hybridizes to complementary oligonucleotides obeying the watson–crick hydrogen–bonding rules," *Nature*, 1993, 365, 566–568.

Frimodt–Møller, N., et al., "The mouse pertonitis/sepsis model," *Handbook of Animal Models of Infection*, Chap. 14, 1999, 127–136.

Giwercman, B., et al., "Rapid emergence of resistance in *Pseudomonas aeruginosa* in cystic fibrosis patients due to in–vivo selection of stable partially derepressed β–lactamase producing strains," *J. Anmtimicrob Chemother*, 1990, 26, 247–259.

Good, Liam, et al., "Antisense inhibition of gene expression in bacteria by PNA targeted to mRNA," *Nature Biotechnology*, 1998, 16, 355–358.

Good, Liam, et al., "Inhibition of translation and bacterial growth by peptide nucleic acid targeted to ribosomal RNA," *Proc. Natl. Acad. Sci USA*, 1998, 95, 2073–2076.

Gopher, A., et al., "Determination of fructose metabolic pathways in normal and fructose–intolerant children: a $^{13}$C NMR study using [U–$^{13}$C]fructose," *Proc. Natl. Acad. Sci. USA*, 1990, 87, 5449–5453.

Hanvey, J.C., et al., "Antisense and antigene properties of peptide nucleic acids," *Science*, 1992, 258, 1481–1485.

Hiramatsu, K., et al., "Dissemination in Japanese hospitals of strains of staphylococcus aureus heterogeneously resistant to vancomycin," *Lancet*, 1997, 350, 1670–1673.

Hsueh, P., "Persistence of a multidrug–resistant *psuedomanas aeruginosa* clone in an intensive care burn unit," *J. Clin. Microbiol*, 1998, 36(5), 1347–1351.

Johnson, A.P., "Intermediate vancomycin resistance in *staphylococcus aureus*: a major threat or a minor inconvenience?," *J. Antimicrob Chemother*, 1998, 42, 289–291.

Knudsen, H., et al., "Antisense properties of duplex–and triplex–forming PNAs," *Nucleic Acids Res.*, 1996, 24(5), 494–500.

Lepelletier, D., et al., *Escherichia coli*: epidemiology and analysis of risk factors for infections caused by resistant strains, *Clin. Infect. Dis.*, 1999, 3, 548–552.

Lewis, J.G., et al., "A serum–resistant cytofectin for cellular delivery of antisense oligodeoxynucleotides and plamsid DNA," *Proc. Natl. Acad. Sci. USA*, 1996, 93, 3176–3181.

Livermore, D., "Multiresistance and 'superbugs'," *Commun. Dis. Public Health*, 1998, 1(2), 74–78.

Livermore, D.M., "Acquired carbapenemases," *J. Antimicrob Chemother*, 1997, 39, 673–676.

Mcneeley, D.F., et al., "An investigation of vancomycin–resistanct *enterococus faecium* within the pediatric service of a large urban medical center," *Pediatr Infect. Dis. J.*, 1998, 17, 184–188.

Meyer, O., et al., "cationic lipsomes coated with polyethylene glycol as carriers for oligonucleotides," *J. Biol. Chem.*, 1998, 273 (25), 15621–15627.

Nielsen, P.E., et al., "Peptide nucleic acid (:PNA), a DNA mimic with a pseudopeptide backbone," *Chemical Society Reviews*, 1997, 73–78.

Nielsen, P.E., et al., "Sequence–selevtive recognition of DNA by strand displacement with a thymine–substituted polyamide," *Science*, 1991, 254, 1497–1500.

Nyce, J.W., et al., "DNA antisense therapy for asthma in an animal model," *Nature*, 997, 385, 721–725.

Northey, D., et al., "Microbial surveillance in a surgical intensive care unit," *Surg. Gynaecol Obstet.*, 1974, 140(3), 321–325.

Pooga, M., et al., "Cell penetrating PNA constructs regulate galanin receptor levels and modifiy pain transmission in vivo," *Nature Biotechnology*, 1998, 16, 857–861.

Porter, E.A., et al., "Non–haemolytic β–amino–acid oligomers," *Nature*, 2000, 404, 565.

Richards, M.J., et al., "Nosocomial infections in medical intensive care units in the United States," *Crt Care Med.*, 1999, 27 (5), 887–892.

Vincent, J., et al., "The prvalence of nosocomial infection in intensive care units in Europe," *JAMA*, 1995, 274 (8), 639–644.

Zervos, M., "Vancomycin–resistant enterococcus faecium infections in the ICU and quinupristin/dalfopristin," *New Horizons*, 1996, 4(3), 385–392.

* cited by examiner

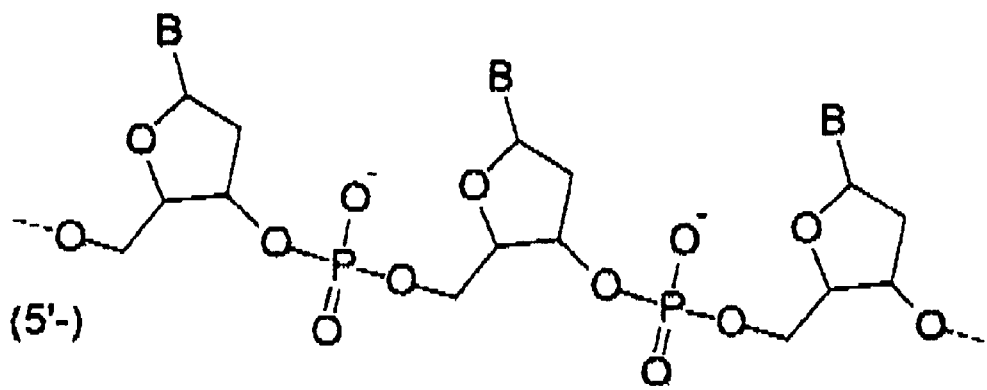
DNA
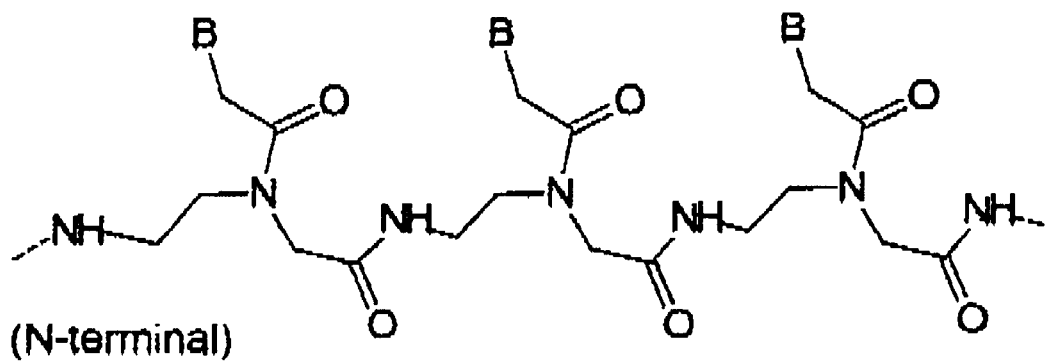
PNA
Figure 1

```
  1 AGATCTTAAA TGCCATTGTG ATGATCTCCT TATCACCCGT CACTCTGACG
 51 GGTATATCAA TGCGTCTGGC TTGCCTTTAT ACTACCGCGC GTTTGTTTAT
101 AAACTGCCCA AATGAAACTA AATGGGAAAT TTCCAGTGAA GTTCGTAAAG
151 TATTTTTTGA TCCTTGCAGT CTGTTGCATT CTGCTGGGAG CAGGCTCGAT
201 TTATGGCCTA TACCGCTACA TCGAGCCACA ACTGCCGGAT GTGGCGACAT
251 TAAAAGATGT TCGCCTGCAA ATTCCGATGC AGATTTACAG CGCCGATGGC
301 GAGCTGATTG CTCAATACGG TGAGAAACGT CGTATTCCGG TTACGTTGGA
351 TCAAATCCCA CCGGAGATGG TGAAAGCCTT TATCGCGACA GAAGACAGCC
401 GCTTCTACGA GCATCACGGC GTTGACCCGG TGGGGATCTT CCGTGCAGCA
451 AGCGTGGCGC TGTTCTCCGG TCACGCGTCA CAAGGGGCAA GTACCATTAC
501 CCAGCAGCTG GCGAGAAACT TCTTCCTCAG TCCAGAACGC ACGCTGATGC
551 GTAAGATTAA GGAAGTCTTC CTCGCGATTC GCATTGAACA GCTGCTGACG
601 AAAGACGAGA TCCTCGAGCT TTATCTGAAC AAGATTTACC TTGGTTACCG
651 CGCCTATGGT GTCGGTGCTG CGGCACAAGT CTATTTCGGA AAAACGGTCG
701 ACCAACTGAC GCTGAACGAA ATGGCGGTGA TAGCCGGGCT GCCGAAAGCG
751 CCTTCCACCT TCAACCCGCT CTACTCGATG GATCGTGCCG TCGCGCGGCG
801 TAACGTCGTG CTGTCGCGGA TGCTGGATGA AGGGTATATC ACCCAACAAC
851 AGTTCGATCA GACACGCACT GAGGCGATTA ACGCTAACTA TCACGCGCCG
901 GAGATTGCTT TCTCTGCGCC GTACCTGAGC GAAATGGTGC GCCAGGAGAT
951 GTATAACCGT TATGGCGAAA GTGCCTATGA AGACGGTTAT CGCATTTACA
1001 CCACCATCAC CCGCAAAGTG CAGCAGGCCG CGCAGCAGGC GGTACGTAAT
1051 AACGTGCTGG ACTACGACAT GCGCCACGGC TATCGCGGCC CGGCAAATGT
1101 GCTGTGGAAA GTGGGCGAGT CGGCGTGGGA TAACAACAAG ATTACCGATA
1151 CGCTGAAGGC GCTGCCAACC TATGGTCCGC TGCTGCCTGC CGCAGTCACC
1201 AGCGCCAATC CTCAGCAAGC GACGGCGATG CTGGCGGACG GGTCGACCGT
1251 CGCATTGAGT ATGGAAGGCG TTCGCTGGGC GCGTCCTTAC CGTTCGGATA
1301 CTCAGCAAGG ACCGACGCCG CGTAAAGTGA CCGATGTTCT GCAAACGGGT
```

Figure 3A

1351 CAGCAAATCT GGGTTCGTCA GGTTGGCGAT GCATGGTGGC TGGCACAAGT

1401 GCCGGAAGTG AACTCGGCGC TGGTGTCGAT CAATCCGCAA AACGGTGCCG

1451 TTATGGCGCT GGTCGGTGGC TTTGATTTCA ATCAGAGCAA GTTTAACCGC

1501 GCCACCCAGG CACTGCGTCA GGTGGGTTCC AACATCAAAC CGTTCCTCTA

1551 CACCGCGGCG ATGGATAAAG GTCTGACGCT GGCAAGTATG TTGAACGATG

1601 TGCCAATTTC TCGCTGGGAT GCAAGTGCCG GTTCTGACTG GCAGCCGAAG

1651 AACTCACCAC CGCAGTATGC TGGTCCAATT CGCTTACGTC AGGGGCTGGG

1701 TCAGTCGAAA AACGTGGTGA TGGTACGCGC AATGCGGGCG ATGGGCGTCG

1751 ACTACGCTGC AGAATATCTG CAACGCTTCG GCTTCCCGGC ACAAAACATT

1801 GTCCACACCG AATCGCTGGC GCTGGGTTCA GCGTCCTTCA CCCCAATGCA

1851 GGTGGCGCGC GGCTACGCGG TCATGGCGAA CGGCGGCTTC CTGGTGGACC

1901 CGTGGTTTAT CAGCAAAATT GAAAACGATC AGGGCGGCGT GATTTTCGAA

1951 GCGAAACCGA AGTAGCCTG CCCGGAATGC GATATTCCGG TGATTTACGG

2001 TGATACGCAG AAATCGAACG TGCTGGAAAA TAACGATGTT GAAGATGTCG

2051 CTATCTCCCG CGAGCAGCAG AATGTTTCTG TACCAATGCC GCAGCTGGAG

2101 CAGGCAAATC AGGCGTTAGT GGCGAAGACT GGCGCGCAGG AGTACGCACC

2151 GCACGTCATC AACACTCCGC TGGCATTCCT GATTAAGAGT GCTTTGAACA

2201 CCAATATCTT TGGTGAGCCA GGCTGGCAGG GTACTGGCTG GCGTGCAGGT

2251 CGTGATTTGC AGCGTCGCGA TATCGGCGGG AAAACCGGGA CCACTAACAG

2301 TTCGAAAGAT GCGTGGTTCT CGGGTTACGG TCCGGGCGTT GTGACCTCGG

2351 TCTGGATTGG CTTTGATGAT CACCGTCGTA ATCTCGGTCA TACAACGGCT

2401 TCCGGAGCGA TTAAAGATCA GATCTCAGGT TACGAAGGCG GTGCCAAGAG

2451 TGCCCAGCCT GCATGGGACG CTTATATGAA AGCCGTTCTT GAAGGTGTGC

2501 CGGAGCAGCC GCTGACGCCG CCACCGGGTA TTGTGACGGT GAATATCGAT

2551 CGCAGCACCG GCAGTTAGC TAATGGTGGC AACAGCCGCG AAGAGTATTT

2601 CATCGAAGGT ACGCAGCCGA CACAACAGGC AGTGCACGAG GTGGGAACGA

2651 CCATTATCGA TAATGGCGAG GCACAGGAAT TGTTCTGA

Figure 3B

```
   1 TGCTGGTCGC AGAGAGTCTG TACCGGGCGT GGAGCATCAC CACCAACCAT
  51 CCTTATCACC GTGAGTGATA AGGGAGCTTT GAGTAGAAAA CGCAGCGGAT
 101 GAAACTACAG AACTCTTTTC GCGACTATAC GGCAGAGTCC GCGCTGTTTG
 151 TGCGCCGGGC GCTGGTCGCC TTTTTGGGGA TTTTGCTGCT GACCGGCGTG
 201 CTTATCGCCA ACCTGTATAA TCTGCAAATT GTTCGCTTTA CCGACTACCA
 251 GACCCGCTCT AATGAAAACC GCATTAAGCT GGTGCCTATC GCGCCCAGCC
 301 GCGGCATTAT CTACGATCGT AACGGTATCC CTCTGGCCCT CAACCGCACT
 351 ATCTACCAGA TAGAAATGAT GCCGGAGAAA GTCGATAACG TGCAGCAAAC
 401 GCTGGACGCT TTGCGCAGCG TGGTAGATCT GACCGATGAC GATATTGCTG
 451 CATTCCGAAA AGAGCGCGCA CGTTCACACC GTTTCACCTC TATTCCGGTG
 501 AAAACTAACC TGACCGAAGT ACAAGTAGCT CGCTTTGCCG TCAATCAGTA
 551 CCGTTTTCCG GGTGTCGAAG TTAAAGGCTA TAAACGTCGT TACTATCCTT
 601 ACGGTTCGGC GTTGACCCAC GTCATCGGCT ATGTGTCGAA AATCAACGAT
 651 AAAGACGTCG AACGCCTGAA TAATGACGGC AAACTGGCCA ACTATGCGGC
 701 AACGCATGAT ATCGGTAAGC TGGGCATTGA GCGTTACTAT GAAGATGTGC
 751 TGCACGGTCA GACCGGTTAT GAAGAGGTTG AAGTTAACAA CCGTGGGCGT
 801 GTTATTCGCC AGTTAAAAGA AGTACCACCG CAAGCCGGAC ACGATATTTA
 851 CCTGACGCTG GATCTCAAAC TCCAGCAATA TATTGAAACG CTGCTGGCGG
 901 GTAGCCGCGC AGCTGTGGTA GTCACCGATC CGCGTACAGG TGGGGTGCTG
 951 GCGCTGGTTT CCACGCCTAG TTATGACCCA AACTTGTTTG TTGACGGTAT
1001 CTCCAGCAAA GATTATTCCG CCTTGTTGAA CGATCCGAAT ACACCGCTGG
1051 TGAACCGCGC CACACAGGGG GTTTATCCTC CCGCGTCTAC AGTTAAACCC
1101 TATGTGGCGG TTTCGGCATT GAGCGCCGGG GTGATCACGC GCAATACGAC
1151 GCTGTTTGAC CCAGGCTGGT GGCAACTGCC AGGTTCGGAA AAACGTTATC
1201 GTGACTGGAA AAAATGGGGC CACGGGCGTC TGAATGTCAC AAGATCGCTG
1251 GAAGAATCTG CGGATACCTT CTTCTATCAG GTGGCCTACG ATATGGGGAT
1301 CGATCGCCTC TCCGAATGGA TGGGTAAATT CGGTTATGGT CATTACACCG
```

Figure 4A

```
1351 GTATCGACCT GGCGGAAGAA CGTTCCGGCA ACATGCCTAC CCGCGAATGG
1401 AAACAGAAAC GCTTTAAAAA ACCGTGGTAT CAGGGTGACA CCATTCCGGT
1451 TGGTATCGGT CAGGGTTACT GGACAGCGAC CCCAATCCAG ATGAGTAAGG
1501 CACTGATGAT CCTGATTAAT GACGGTATCG TGAAGGTTCC TCATTTGCTG
1551 ATGAGCACCG CCGAAGACGG CAAACAGGTG CCATGGGTAC AGCCGCATGA
1601 ACCGCCCGTC GGCGATATTC ATTCCGGTTA CTGGGAGCTG GCGAAAGACG
1651 GTATGTACGG TGTTGCTAAC CGCCCTAACG GTACGGCGCA TAAATACTTT
1701 GCTAGCGCAC CGTACAAAAT TGCGGCGAAA TCCGGTACCG CTCAGGTCTT
1751 CGGTCTGAAA GCGAACGAAA CCTATAATGC GCACAAAATT GCCGAGCGTT
1801 TACGTGACCA CAAACTGATG ACCGCCTTTG CGCCATACAA CAATCCGCAA
1851 GTGGCTGTCG CCATGATTCT GGAGAACGGT GGTGCGGGTC CGGCGGTTGG
1901 TACACTGATG CGCCAGATCC TCGACCACAT TATGCTGGGT GATAACAACA
1951 CCGATCTGCC TGCGGAAAAT CCAGCGGTTG CCGCAGCGGA GGACCATTAA
```

Figure 4B

MODIFIED PEPTIDE NUCLEIC ACID (PNA) MOLECULES

CROSS REFERENCE TO RELATED APPLICATIONS

This application claims priority to Danish Application No. PA 1999 01467 filed Oct. 13, 1999; U.S. Provisional Application No. 60/159,684 filed Oct. 15, 1999; Danish Application No. PA 1999 01735 filed Dec. 3, 1999; Danish Application No. PA 2000 00522 filed Mar. 28, 2000; U.S. Provisional Application No. 60/211,758 filed Jun. 14, 2000; Danish Application No. PA 1999 01471 filed Oct. 13, 1999; U.S. Provisional Application No. 60/159,679 filed Oct. 15, 1999, Danish Application No. PA 1999 01734 filed Dec. 3, 1999; Danish Application No. PA 2000 00670 filed Apr. 19, 2000; U.S. Provisional Application No. 60/211,878 filed Jun. 14, 2000; Danish Application No. PA 2000 00671 filed Apr. 19, 2000; and U.S. Provisional Application No. 60/211,435 filed Jun. 14, 2000, each of which are incorporated herein by reference in their entirety.

FIELD OF THE INVENTION

The present invention relates to novel drugs for use in combating, for example, infectious microorganisms, particularly bacteria. More specifically, the invention relates to peptide nucleic acid (PNA) sequences that are modified in order to obtain novel PNA molecules which exhibit enhanced anti-infective properties.

BACKGROUND OF THE INVENTION

The discovery of penicillin in the 1940's marked the beginning of the search for new antibiotics. Many antibiotics have been discovered or developed from existing drugs, and the number of antibiotic drugs currently used by clinicians is more than 100. Many strains of bacteria have, unfortunately, become resistant to one or more of the currently available antibiotics.

Most antibiotics are products of natural microbic populations and resistant traits found in these populations can disseminate between species and appear to have been acquired by pathogens under selective pressure from antibiotics used in agriculture and medicine (Davis et al., Science, 1994, 264, 375). Antibiotic resistance may develop in bacteria harbouring genes that encode enzymes that either chemically alter or degrade antibiotics. Resistant bacteria may also encode enzymes that make the cell wall impervious to antibiotics or encode efflux pumps that eject antibiotics from the cell before the antibiotics can exert their effects. Due to the emergence of antibiotic-resistant bacterial pathogens, a need for new therapeutic strategies has arisen. One strategy for avoiding problems caused by resistance genes is the development of anti-infective drugs from novel chemical classes for which specific resistance traits do not exist.

Antisense agents offer a novel strategy for combatting disease, as well as opportunities to employ new chemical classes in drug design. Oligonucleotides can interact with native DNA and RNA in several ways, including duplex formation between an oligonucleotide and a single-stranded nucleic acid and triplex formation between an oligonucleotide and double-stranded DNA to form a triplex structure. The use of anti-sense methods in basic research has been encouraging, and antisense oligonucleotide drug formulations that target viral and disease-causing human genes are progressing through clinical trials. Antisense inhibition of bacterial genes could also have wide application; however, few attempts have been made to extend antisense technology to bacteria.

Peptide nucleic acids (PNA) are similar to oligonucleotides and oligonucleotide analogs and may mimic DNA and RNA. The deoxyribose backbone of DNA is replaced in PNA by a pseudo-peptide backbone (Nielsen et al., Science, 1991, 254, 1475; see FIG. 1). Each subunit, or monomer, has a naturally occurring or non-naturally occurring nucleobase attached to the backbone. One such backbone consists of repeating units of N-(2-aminoethyl)glycine linked through amide bonds. PNA hybridizes to complementary nucleic acids through Watson and Crick base pairing and helix formation results (Egholm et al., Nature, 1993, 365, 566). The Pseudo-peptide backbone provides superior hybridization properties (Egholm et al., Nature, 1993, 365, 566), resistance to enzymatic degradation (Demidov et al., P.E. Biochem. Pharmacol., 1994, 48, 1310) and access to a variety of chemical modifications (Nielsen et al., Chemical Society Reviews, 1997, 73).

PNA binds both DNA and RNA to form PNA/DNA or PNA/RNA duplexes. The resulting PNA/DNA or PNA/RNA duplexes are bound with greater affinity than corresponding DNA/DNA or DNA/RNA duplexes, as determined by Tms. The thermal stability of PNA/DNA and PNA/RNA duplexes could be due to the lack of charge repulsion in the neutral backbone of PNA. In addition to increased affinity, PNA has also been shown to hybridize to DNA with increased specificity, as compared to DNA/DNA duplexes. When a PNA/DNA duplex mismatch is melted relative to a DNA/DNA duplex, an 8 to 20° C. drop in the $T_m$ results. Furthermore, homopyrimidine PNA oligomers form extremely stable $PNA_2$-DNA triplexes with sequence-complementary targets in DNA or RNA oligomers. Finally, PNAs may bind to double-stranded DNA or RNA by helix invasion.

One advantage of PNA, as compared to oligonucleotides, is the nuclease and protease reisitance of the PNA polyamide backbone. PNA is not recognized by either nucleases or proteases and is thus not susceptible to cleavage; consequently, PNAs are resistant to degradation by enzymes, unlike nucleic acids and peptides. In antisense applications, target-bound PNA can cause steric hindrance of DNA and RNA polymerases, reverse transcripase, telomerase and ribosomes (Hanvey et al., Science, 1992, 258, 1481; Knudsen et al., Nucleic Acids Res., 1996, 24, 494; Good at el., Proc. Natl. Acad. Sci USA, 1998, 95, 2073; Good, et al., Nature Biotechnology, 1998, 16, 355).

A general difficulty in the use of antisense agents is cell uptake. A variety of strategies to improve uptake have been explored and reports of improved uptake into eukaryotic cells using lipids (Lewis et al., Proc. Natl. Acad. Sci. USA, 1996, 93, 3176), encapsulation (Meyer et al., J Biol. Chem., 1998, 273, 15621) and carrier strategies (Nyce et al., Nature, 1997, 385, 721; Pooga et al., Nature Biotechnology, 1998, 16, 857) have been made. WO 99/05302 discloses a PNA conjugate consisting of PNA and the transporter peptide transportan, in which the peptide can be used for transport cross a lipid membrane and for delivery of the PNA into interactive contact with intracellular polynucleotides. U.S. Pat. No. 5,777,078 discloses a pore-forming compound which comprises a delivery agent that recognizes the target cell and is linked to a pore-forming agent, such as a bacterial exotoxin. The compound is administered together with a drug such as PNA.

PNAs have unique advantages as an antisense agent for microorganisms. PNA-based antisense agents can control cell growth and growth phenotypes when targeted to *Escherichia coli* rRNA and mRNA (Good et al., *Proc. Natl. Acad. Sci USA*, 1998, 95, 2073; Good et al., *Nature Biotechnology*, 1998, 16, 355; and WO 99/13893).

None of the cited disclosures discuss methods of transporting PNA across the bacterial cell wall and membrane. Poor uptake of PNA is expected because bacteria have stringent barriers against entry of foreign molecules and antisense oligomer-containing nucleobases appear to be too large for efficient uptake. The results obtained by Good and Nielsen (Good et al., *Proc. Natl. Acad. Sci USA*, 1998, 95, 2073; Good, et al., *Nature Biotechnology*, 1998, 16, 355) indicate that PNA oligomers enter bacterial cells poorly by passive diffusion across the lipid bilayers.

U.S. Pat. No. 5,834,430 discloses the use of potentiating agents, such as short cationic peptides, in the potentiation of antibiotics. The agent and the antibiotic are co-administered. WO 96/11205 discloses PNA conjugates, wherein a conjugated moiety may be placed on terminal or non-terminal parts of the backbone of PNA in order to functionalize the PNA. The conjugated moieties may be reporter enzymes or molecules, steroids, carbohydrate, terpenes, peptides, proteins, etc. The conjugates possess improved transfer properties for crossing cellular membranes; however, WO 96/11205 does not disclose conjugates that can cross bacterial membranes.

WO 98/52614 discloses a method of enhancing transport over biological membranes, e.g., a bacterial cell wall. According to this publication, biologically active agents such as PNA may be conjugated to a transporter polymer in order to enhance transmembrane transport. The transporter polymer consists of 6–25 subunits, at least 50% of which contain a guanidino or amidino side chain moiety, and wherein at least 6 contiguous subunits contain guanidino and/or amidino side chains. A preferred transporter polymer is a polypeptide containing 9-arginine. Despite the promising results obtained with the use of the PNA technology, there is a great need in the art for development of new PNA antisense drugs that are effective in combatting microorganisms.

SUMMARY OF THE INVENTION

The present invention relates to a new strategy for combatting bacteria. Antisense PNA can inhibit the growth of bacteria; however, due to slow diffusion of PNA across the bacterial cell wall, the use of PNA as an antibiotic has not been possible. According to the present invention, a practical application for PNA in combatting bacteria can be achieved by modifying the PNA through linkage of a peptide or peptide-like sequence that enhances the activity of the PNA.

Surprisingly, it has been demonstrated that incorporation of a peptide in PNA results in an enhanced anti-infective effect. An important feature of the modified PNA molecules is a pattern comprising positively charged and lipophilic amino acids or amino acid analogues. An anti-infective effect is found with different orientations of the peptide relative to the PNA sequence. Thus, one aspect of the present invention is directed to a modified PNA molecule, and pharmaceutically acceptable salt thereof, of Formula I:

Peptide-L-PNA          (I)

wherein L is a linker or a bond, Peptide is any amino acid sequence, and PNA is a Peptide Nucleic Acid.

More particularly, the present invention is directed to a modified PNA molecule of Formula I Peptide-L-PNA          (I)

wherein Peptide is a cationic peptide or cationic peptide analogue or a functionally similar moiety, the peptide or peptide analogue having the Formula II:

$$C\text{-}(B\text{-}A)_n\text{-}D, \qquad (II)$$

wherein A is from 1 to 8 non-charged amino acids and/or amino acid analogs, B is from 1 to 3 positively charged amino acids and/or amino acid analogs, C is from 0 to 4 non-charged amino acids and/or amino acid analogs, D is from 0 to 3 positively charged amino acids and/or amino acid analogs, n is 1–10, and the total number of amino acids and/or amino acid analogs is from 3 to 20.

In one embodiment, the Peptide of the present invention comprises from 2 to 60 amino acids. The amino acids can be negatively charged, non-charged, or positively charged naturally-occurring, rearranged, or modified amino acids. In a preferred embodiment of the invention, the peptide comprises from 2 to 18 amino acids, and most preferably from 5 to 15 amino acids.

In another preferred embodiment of the invention, A in Formula II comprises from 1 to 6 non-charged amino acids and/or amino acid analogs and B comprises 1 or 2 positively charged amino acids and/or amino acid analogs. In another embodiment, A comprises from 1 to 4 non-charged amino acids and/or amino acid analogs and B comprises 1 or 2 positively charged amino acids and/or amino acid analogs.

In a preferred embodiment of the invention, the modified PNA molecules of Formula I are used, for example, in the treatment or prevention of infections caused by *Escherichia coli* or vancomycin-resistant enterococci such as *Enterococcus faecalis* and *Enterococcus faecium* or infections caused by methicillin-resistant and methicillin-vancomycin-resistant *Staphylococcus aureus*.

The peptide moiety in a modified PNA molecule is linked to the PNA sequence via the amino (N-terminal) or carboxy (C-terminal) end. In a preferred embodiment, the peptide is linked to the PNA sequence via the carboxy end.

In another aspect of the invention, modified PNA molecules are used in the manufacture of medicaments for the treatment or prevention of infectious diseases or for disinfecting non-living objects. In a further aspect, the invention concerns a composition for treating or preventing infectious diseases or disinfecting non-living objects. In yet another aspect, the invention concerns the treatment or prevention of infectious diseases or treatment of non-living objects.

In yet a further aspect, the present invention is directed to a method of identifying specific advantageous antisense PNA sequences that may be used in the modified PNA molecule according to the invention.

In yet a further aspect, the present invention relates to other antisense oligonucleotides with the ability to bind to both DNA and RNA.

Oligonucleotide analogs are oligomers having a sequence of nucleotide bases (nucleobases) and a subunit-to-subunit backbone that allows the oligomer to hybridize to a target sequence in an mRNA by Watson-Crick base pairing, to form an RNA/Oligomer duplex in the target sequence. The oligonucleotide analog may have exact sequence complementarity to the target sequence or near complementarity, as long as the hybridized duplex structure formed has sufficient stability to block or inhibit translation of the mRNA containing target sequence.

Oligonucleotide analogs of the present invention are selected from the group consisting of Locked Nucleoside Analogues (LNA) as described in International PCT Publication WO99/14226, oligonucleotides as described in International PCT Publication WO98/03533 or antisense oligomers, in particular morpholino analogs as described in International PCT Publication WO98/32467.

PCT Publication WO99/14226, WO98/03533 and WO98/32467 are all incorporated by reference.

Thus, further preferred compounds of the invention are modified oligonucleotides of the Formula (III):

wherein L is a linker or a bond; Peptide is any amino acid sequence and Oligon is an oligonucleotide or analog thereof.

BRIEF DESCRIPTION OF THE DRAWINGS

FIG. 1 shows representative chemical structures of DNA and PNA oligomers.

FIGS. 3A and 3B show the nucleotide sequence of the mrcA (ponA) gene encoding PBP1A. The sequence of the gene (accession number X02164) was obtained from the EMBL sequence database (Heidelberg, Germany) (Broome-Smith et al., *Eur J Biochem*, 1985, 147, 437). Two possible start codons have been identified (bolded). Bases 1–2688 are shown (ending with stop codon).

FIGS. 4A and 4B show the nucleotide sequence of the mrdA gene encoding PBP2. The sequence (accession number AE000168, bases 4051–5952, numbered 1–2000) was obtained from the *E. coli* genome database at the NCBI (Genbank, National Center for Biotechnology Information, USA). The start codon is bolded.

DESCRIPTION OF PREFERRED EMBODIMENTS OF THE INVENTION

Figure 2:
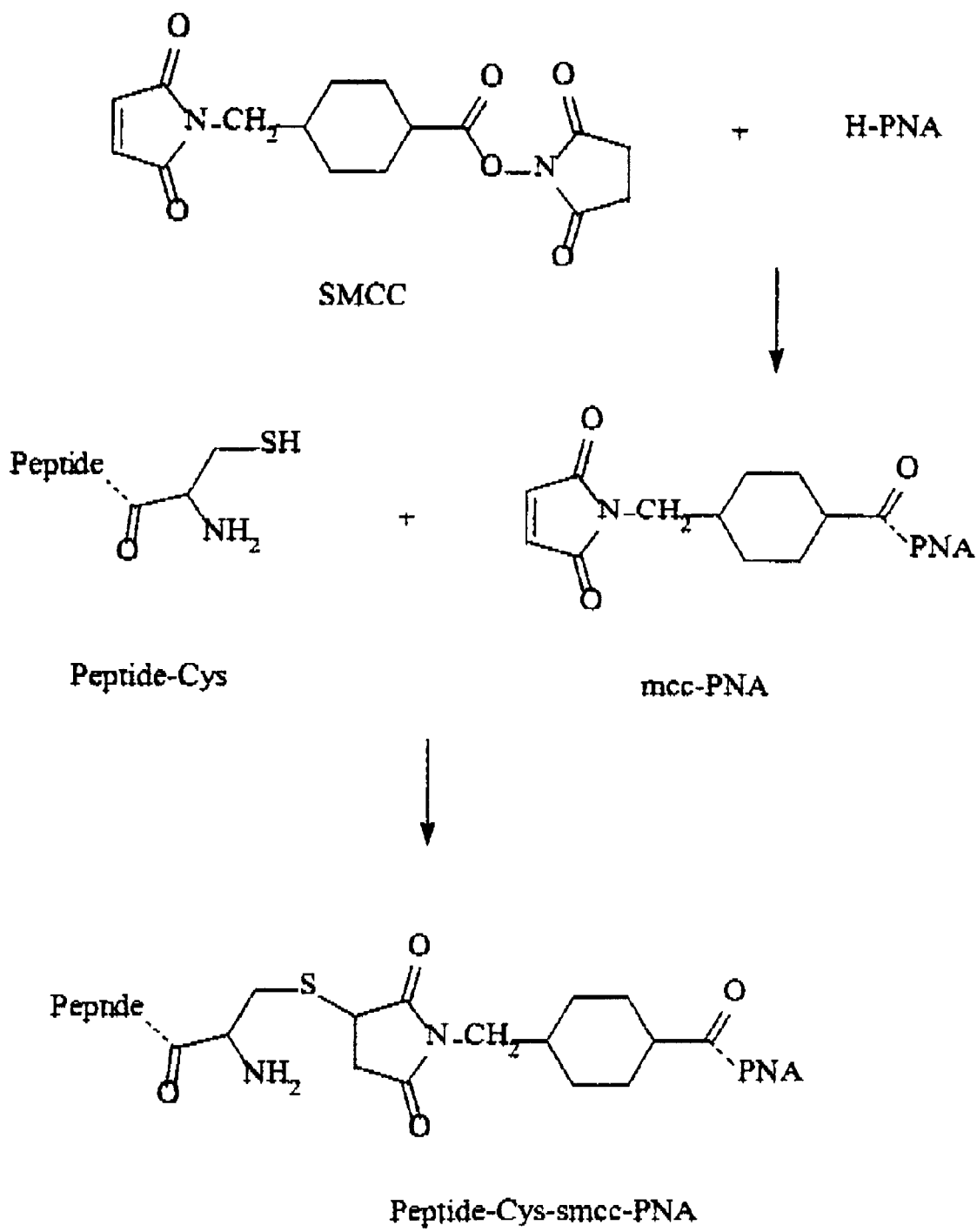
FIG. 2 is a schematic showing a representative conjugation using SMCC.

The present invention relates, in part, to a modified oligonucleotide of Formula III:

wherein L is a linker or a bond, Peptide is any amino acid sequence, and Oligon is an oligonucleotide or analog thereof.

Oligons useful for the invention include, but are not limited to, oligonucleotide analogs such as, for example, Locked Nucleoside Analogues (LNA), as described in International PCT Publication WO99/14226, or analogs as described in International PCT Publication WO98/03533, or morpholino analogs as described in International PCT Publication WO98/32467, each of which are incorporated herein by reference in their entirety.

Antisense PNAs can inhibit bacterial gene expression with gene and sequence specificity (Good et al., *Proc. Natl. Acad. Sci USA*, 1998, 95, 2073; Good et al., *Nature Biotechnology*, 1998, 16, 355; and WO 99/13893). Antisense PNAs may prove to be a practical tool for functional genomics and a source of novel antimicrobial drugs. However, improvements in standard PNA techniques are required in order to increase antisense potencies. The major limit to antisense activity appears to be cellular entry. Bacteria effectively exclude the entry of large molecular weight foreign compounds, and previous results of in vitro and cellular assays seem to demonstrate that the cell barrier restricts antisense effects. Accordingly, the present invention concerns strategies to improve the activity of antisense PNAs.

Without being bound by theory, it is believed that short cationic peptides lead to improved PNA uptake over the bacterial cell wall. It is believed that the short peptides act by penetrating the cell wall and allowing the modified PNA molecule to cross the cell wall and gain access to structures inside the cell, such as the genome, mRNAs, the ribosome, etc. Improved accessibility to the nucleic acid target or improved binding of the PNA may also add to the overall effect observed.

According to one aspect of the invention, nanomolar concentrations of PNA molecules modified with short, activity-enhancing peptides enable specific and efficient inhibition of bacterial gene expression. Antisense potencies in this concentration range are consistent with practical applications of the technology. It is believed that the present invention demonstrates for the first time that peptides with a certain pattern of cationic and lipophilic amino acids can be used as carriers to deliver agents and other compounds into micro-organisms, such as bacteria. Further, the present invention has made it possible to administer PNA in an efficient concentration that is also acceptable to the patient. Accordingly, the present invention concerns novel modified PNA molecules of the formula:

 wherein

L is a linker or a bond, PNA is a peptide nucleic acid sequence, and Peptide is a cationic peptide or peptide analog or a functionally similar moiety, the peptide or peptide analog preferably having the formula:

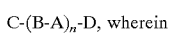, wherein

A comprises from 1 to 8 non-charged amino acids and/or amino acid analogs, B comprises from 1 to 3 positively charged amino acids and/or amino acid analogs, C comprises from 0 to 4 non-charged amino acids and/or amino acid analogs, D comprises from 0 to 3 positively charged amino acids and/or amino acid analogs, n is 1–10, and the total number of amino acids and/or amino acid analogs is from 3 to 20.

A preferred group of modified PNA molecules is the group wherein A comprises from 1 to 6 non-charged amino acids and/or amino acid analogs and B comprises 1 or 2 positively charged amino acids and/or amino acid analogs. In another preferred group, A comprises from 1 to 4 non-charged amino acids and/or amino acid analogs and B comprises 1 or 2 positively charged amino acids and/or amino acid analogs.

The terms "cationic amino acids and amino acid analogs" and "positively charged amino acids and amino acid analogs" include, but are not limited to, any natural or non-naturally occurring amino acids or amino acid analogs that have a positive charge at physiological pH. Similarly, the term "non-charged amino acids or amino acid analogs" includes any natural or non-naturally occurring amino acids or amino acid analogs that have no charge at physiological pH. Positively charged amino acids and amino acid analogs include lysine (Lys, K), arginine (Arg, R), diamino butyric acid (DAB), and ornithine (Orn). The skilled artisan is aware of further positively charged amino acids and amino acid analogs.

The term "cationic peptide" includes any natural or non-naturally occurring peptide that has a positive charge at physiological pH.

The term "peptide analog" includes any natural or non-naturally occurring peptide, or derivative thereof.

The non-charged amino acids and amino acid analogs include, but are not limited to, the naturally occurring amino acids alanine (Ala, A), valine (Val, V), leucine (Leu, L), isoleucine (Ile, I), proline (Pro, P), phenylanaline (Phe, F), tryptophan (Trp, W), methionine (Met, M), glycine (Gly, G), serine (Ser, S), threonine (Thr, T), cysteine (Cys, C), tyrosine (Tyr, Y), asparagine (Asn, N) and glutamine (Gln, Q), and the non-naturally occurring amino acids 2-aminobutyric acid, β-cyclohexylalanine, 4-chlorophenylalanine, norleucine and phenylglycine. The skilled artisan is aware of additional non-charged amino acids and amino acid analogs. Preferably, the non-charged amino acids and amino acid analogs are selected from the naturally occurring non-polar amino acids Ala, Val, Leu, Ile, Phe, Trp and Met or the non-naturally occurring non-polar amino acids β-cyclohexylalanine, 4-chlorophenylalanine and norleucine.

The term "functionally similar moiety" includes all peptide-like molecules that functionally mimic the Peptide as defined above and thus impart to the PNA molecule the same advantageous properties as the peptides comprising natural and non-natural amino acids as defined above.

Examples of preferred modified PNA molecules according to the invention include, but are not limited to, (Lys Phe Phe)$_3$ Lys-L-PNA and any subunits thereof comprising at least three amino acids. One preferred Peptide is (Lys Phe Phe)$_3$ (SEQ ID NO:1). Others include (Lys Phe Phe)$_2$ Lys Phe (SEQ ID NO:2), (Lys Phe Phe)$_2$ Lys (SEQ ID NO:157), (Lys Phe Phe)$_2$ (SEQ ID NO:3), Lys Phe Phe Lys Phe (SEQ ID NO:4), Lys Phe Phe Lys (SEQ ID NO:5) and Lys Phe Phe. Other preferred Peptides are FFRFFRFFR (SEQ ID NO:6), LLKLLKLLK (SEQ ID NO:7), LLRLLRLLR (SEQ ID NO:8), LLKKLAKAL (SEQ ID NO:9), KRRWPWWP-WKK (SEQ ID NO:10), KFKVKFVVKK (SEQ ID NO:11), LLKLLLKLLLK (SEQ ID NO:12), LLKKLAKALK), and any subunits thereof comprising at least 3 amino acids whereof at least one amino acid is a positively charged amino acid. Also included are derivatives of the peptides having conservative amino acid substitutions, or insertions or deletions.

A third group of preferred Peptides is RRLFPWWWP-FRRVC (SEQ ID NO:14), GRRWPWWPWKWPLIC (SEQ ID NO:15), LVKKVATTLKKIFSKWKC (SEQ ID NO:16), KKFKVKFVVKKC (SEQ ID NO:17) and any subunit thereof comprising at least 3 amino acids whereof at least one amino acid is a positively charged amino acid. A fourth group of preferred Peptides is magainis (Zasloff, *Proc. Natl. Acad. Sci. USA*, 1987, 84, 5449), for instance the synthetic magainin derivative GIGKFLHAAKKFAKAFVAEIMNS-NH$_2$ (SEQ ID NO:158) as well as β-amino-acid oligomers (β-peptides) as described by Porter, et al., *Nature*, 2000, 404, 565.

The number of amino acids in the peptide can be from 3 to 20. Preferably, at least 3 amino acids, at least one of which is a positively charged amino acid, are necessary to obtain the advantageous effect. On the other hand, the upper limit for the number of amino acids in the peptide seems only to be set by the overall size of the PNA molecule. Preferably, the total number of amino acids is 15 or less, more preferably 12 or less, and most preferably 10 or less.

In a preferred embodiment of the invention, the PNA contains from 5 to 20 nucleobases, preferably from 7–15 nucleobases, and most preferably from 8 to 12 nucleobases. In a further preferred embodiment of the invention, the PNA backbone is aminoethylglycine as shown in FIG. 1. PNAs are described in, for example, WO 92/20702 and WO 92/20703, each of which is incorporated herein by reference in its entirety.

The PNA molecule is connected to the Peptide moiety through direct binding or through a linker. A variety of linking groups can be used to connect the PNA with the Peptide. Linking groups are described in, for example, WO 96/11205 and WO98/52614, each of which is incorporated herein by reference in its entirety. Some linking groups may be advantageous in connection with specific combinations of PNA and Peptide.

Preferred linking groups include 8-amino-3,6-dioxaoctanoic acid (ADO), succinimidyl 4-(N-maleimidomethyl)cyclohexane-1-carboxylate (SMCC), 6-aminohexanoic acid (AHEX or AHA), 4-aminobutyric acid, 4-aminocyclohexylcarboxylic acid, succinimidyl 4-(N-maleimidomethyl)cyclohexane-1-carboxy-(6-amido-caproate) (LCSMCC), succinimidyl m-maleimido-benzoylate (MBS), succinimidyl N-ε-maleimido-caproylate (EMCS), succinimidyl 6-(β-maleimido-propionamido) hexanoate (SMPH), succinimidyl N-(α-maleimido acetate) (AMAS), succinimidyl 4-(p-maleimidophenyl)butyrate (SMPB), β-alanine (β.ALA), Phenylglycine (PHG), 4-aminocyclohexanoic acid (ACHC), β-(cyclopropyl) alanine (β.CYPR), amino dodecanoic acid (ADC), polyethylene glycols and amino acids. Any of these groups can be used as a single linking group or together with more groups in creating a suitable linker. Further, the different linking groups can be combined in any order and number in order to obtain different functionalities in the linker arm.

Figure 5:
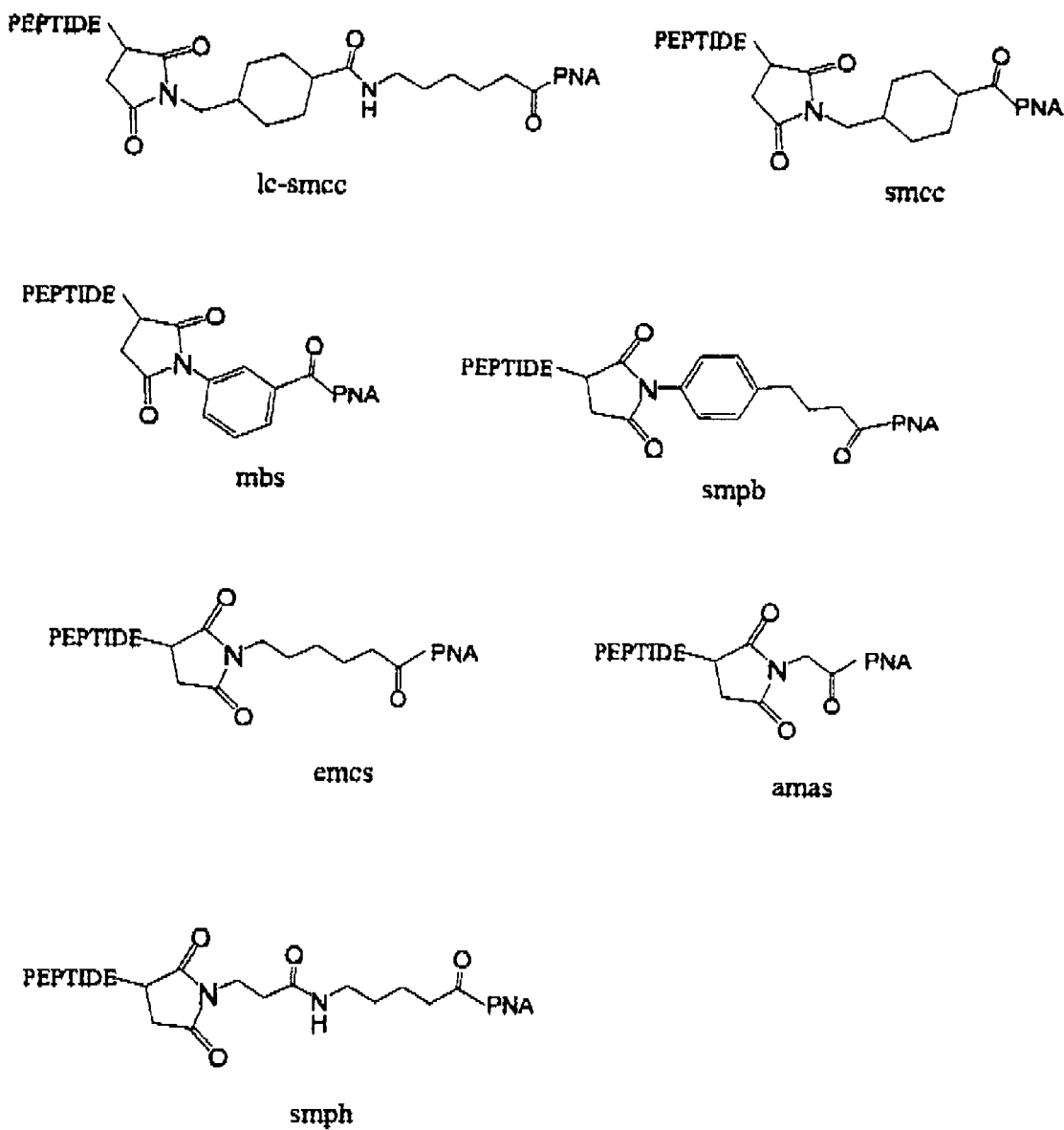
FIG. 5 shows representative chemical structures of different succinimidyl based linking groups used in conjugation of a Peptide and PNA

In a preferred embodiment, the linking group is a combination of the β.ALA linking group or the ADO linking group with any of the other above mentioned linking groups. Thus, preferred linkers include, but are not limited to, -achc-β.ala-, -achc-ado-, -lcsmcc-β.ala-, -mbs-β.ala-, -emcs-β.ala-, -lcsmcc-ado-, -mbs-ado-, -emcs-ado- or -smph-ado-. Most preferred linkers include the following: -achc-β.ala-, -lcsmcc-ado- and -mbs-ado-. When succinimidyl 4-(N-maleimidomethyl)cyclohexane-1-carboxylate (SMCC) is used in the process of linking PNA to the peptide, it is necessary to add a cysteine (C) or a similar thiol containing moiety to the terminal end of the peptide (see FIG. 2). Additionally, amino acids, such as glycine, can be a part of the linker. The chemical structures of the different succinimidyl based linking groups used in the conjugation of the Peptide and PNA is shown in FIG. 5.

The Peptide is normally linked to the PNA sequence via the amino or carboxy end. However, the PNA sequence may also be linked to an internal part of the peptide, or the PNA sequence is linked to a peptide via both the amino and the carboxy end.

The following discussion regarding modified PNA targets is not limited to targets of modified PNA molecules and is equally applicable to targets of the modified oligonucleotides of the invention.

The modified PNA molecules of the present. invention comprise PNA oligomer sequences that are complementary to at least one target nucleotide sequence in a microorganism, such as a bacterium. The target may be a nucleotide sequence of any RNA that is essential for the growth, and/or reproduction of the bacteria. Alternatively, the target may be a gene encoding a factor responsible for resistance to antibiotics. In a preferred embodiment, the functioning of the target nucleotide sequence is essential for the survival of the bacteria and the functioning of the target nucleic acid is blocked by the PNA sequence, in an antisense manner.

The binding of a PNA strand to a DNA or RNA strand can occur in one of two orientations, anti-parallel or parallel. As used in the present invention, the term "complementary" as applied to PNA does not in itself specify the orientation parallel or anti-parallel. It is significant that the most stable orientation of PNA/DNA and PNA/RNA is anti-parallel. In a preferred embodiment, PNA targeted to single- stranded RNA is complementary in an anti-parallel orientation.

In a another preferred embodiment of the invention, a bis-PNA consisting of two PNA oligomers covalently linked to each other is targeted to a homopurine sequence (consisting of only adenine and/or guanine nucleotides) in RNA (or DNA), with which it can form a PNA$_2$-RNA (PNA$_2$-DNA) triple helix.

Potential target genes can be chosen based upon knowledge about bacterial physiology. A target gene can be found among those involved in one of the major process complexes: cell division, cell wall synthesis, protein synthesis (translation), nucleic acid synthesis, fatty acid metabolism, and gene regulation. A target gene can also be involved in antibiotic resistance. A further consideration in selecting target genes is that some physiological processes are primarily active in dividing cells whereas others are active under non-dividing circumstances as well.

Known target proteins in cell wall biosynthesis are penicillin binding proteins, PBPs, the targets of, e.g., the beta-lactam antibiotic penicillin, which are involved in the final stages of cross-linking of the murein sacculus. E. coli has 12 PBPs,- which include the high molecular weight PBPs: PBP1a, PBP1b, PBP1c, PBP2 and PBP3, and seven low molecular weight PBPs: PBP 4–7, DacD, AmpC and AmpH. Only the high molecular weight PBPs are known to be essential for growth and have therefore been chosen as targets for PNA antisense molecules. Protein biosynthesis is an important process throughout the bacterial cell cycle; consequently, targeting enzymes involved in protein biosynthesis is not dependent upon cell division.

Proteins involved in DNA and RNA synthesis are also antibiotic targets. A target protein in DNA synthesis is gyrase, which acts in replication, transcription, repair and restriction. The enzyme consists of two subunits, both of which are candidate targets for PNA. Examples of potential targets primarily activated in dividing cells are rpoD, gyrA, gyrB, (transcription), mrcA (ponA), mrcB (ponB, pbpF), mrdA, ftsI (pbpB) (cell wall biosynthesis), ftsQ, ftsA and ftsZ (cell division). Examples of potential targets also activated in non-dividing cells are infA, infB, infC, tufA/tufB, tsf, fusA, prfA, prfB, and prfC, (translation).

Other potential target genes are antibiotic resistance-genes, with which the skilled artisan is familiar. Examples of such genes include, but are not limited to, genes encoding beta-lactamases and genes encoding chloramphenicol acetyl transferase. PNAs against such resistance genes could be used against resistant bacteria.

A further potential target gene is the acpP gene encoding the acyl carrier protein of E. Coli. ACP (acyl carrier protein) is a small and highly soluble protein, which plays a central role in type I fatty acid synthase systems. Intermediates of long chain fatty acids are covalently bound to ACP by a thioester bond between the carboxyl group of the fatty acid and the thiol group of the phosphopantheteine prosthetic group. ACP is one of the most abundant proteins in E. coli, constituting 0.25% of the total soluble protein (ca $6 \times 10^4$ molecules per cell). The cellular concentration of ACP is regulated, and overproduction of ACP from an inducible plasmid is lethal to E. coli cells.

Infectious diseases are caused by micro-organisms including bacteria, viruses, protozoa, worms and arthropods. PNA can be modified and used to target RNA in such micro-organisms, whether the micro-organisms are sensitive or resistant to antibiotics.

Examples of microorganisms that can be treated in accordance with the present invention include, but are not limited to, Gram-positive bacteria such as Streptococcus, Staphylococcus, Peptococcus, Bacillus, Listeria, Clostridium, Propionebacteria; Gram-negative bacteria such as Bacteroides, Fusobacterium, Escherichia, Klebsiella, Salmonella, Shigella, Proteus, Pseudomonas, Vibrio, Legionella, Haemophilus, Bordetella, Brucella, Campylobacter, Neisseria, Branhamella; and organisms that stain poorly or not at all with Gram's stain such as Mycobacteria, Treponema, Leptospira, Borrelia, Mycoplasma, Clamydia, Rickettsia and Coxiella.

The incidence of multiple antimicrobial resistant bacteria that cause infections in hospitals/intensive care units is increasing. Such bacteria include methicillin-resistant and methicillin-vancomycin-resistant Staphylococcus aureus, vancomycin-resistant enterococci such as Enterococcus faecalis and Enterococcus faecium, penicillin-resistant Streptococcus pneumoniae and cephalosporin and quinolone resistant gram negative rods (coliforms) such as E. coli, Klebsiella pneumoniae, Pseudomonas species and Enterobacter species. Recently, pan antibiotic (including carbapenems) resistant gram negative bacilli have emerged. The rapidity of the emergence of these multiple antibiotic-resistant bacteria is not being matched by the same rate of development of new antibiotics and it is, therefore, conceivable that patients with serious infections will soon no longer be treatable with currently available antimicrobials (Levy, Trends Microbial, 1996; 2, 341; Levy SB. The antibiotic paradox, how miracle drugs are destroying the miracle. New York: Plenum, 1992). Several international reports have highlighted the potential problems associated with the emergence of antimicrobial resistance in many areas of medicine and have also outlined the difficulties in the management of patients with infections caused by these micro-organisms (House of Lords Select Committee on Science and Technology. Resistance to antibiotics and other antimicrobial agents. London: HMSO, 1998; Lepellier et al., Clin Infect Dis, 1999, 3, 548).

Methicillin-resistant S. aureus (MRSA) (Chambers, Clin Microbiol Rev, 10, 781; Elliott, Current Medical Literature-Surgical Infections, 1997, 9), methicillin-vancomycin resistant S. aureus (VMRSA), and vancomycin resistant enterococci (VRE) have emerged as major nosocomial pathogens (House of Lords Select Committee on Science and Technology. Resistance to antibiotics and other antimicrobial agents. London: HMSO, 1998; Arthur et al., Trends Microbiol, 1996, 4, 410; Zervos, New, 1996, 4, 385; Carmelli et al., Arch Intern Med, 1999, 159, 2461). Vancomycin is currently the most reliable treatment for infections caused by MRSA, but the potential transfer of resistance genes from VRE to MRSA may leave few therapeutic options in the future. VRE provide a reservoir of vancomycin resistance genes and can also cause infections in patients with compromised immunity. Some VRE strains exhibit resistance to all major classes of antibiotic and in some hospitals in the United States VRE are responsible for more than 20% of enterococcal infections (Mcneeley et al., Pediatr Infect Dis J, 1998, 17, 184; Carmelli et al., Arch Intern Med, 1999, 159, 2461).

S. aureus, exhibiting intermediate vancomycin resistance (VISA), as well as VMRSA, have now been reported in several centers/hospitals worldwide (Johnson, J Antimicrob Chemother, 1998, 42, 289; Hiramatsu et al., Lancet, 1997, 350, 1670). Of the S. aureus isolates from the U.S.A., Europe, and Japan, 60–72% were MRSA. Multi-drug-resistant MRSA are the most common cause of surgical site infections, comprising 61% of all S. aureus infections, and are a major cause of increased morbidity and mortality of ICU patients (Communicable Disease Report (CDN), 1999, 9, 8; Cookson, *J Hosp Infec*, 1999, 97; Liu et al., *Chong Hua Min Kuo Hsiao Erh Ko I Hsueh Hui Tsa Chih* 1993, 34, 285; Richards et al., *Crit Care Med*, 1999, 5,887).

Coagulase negative staphylococci (CNS), such as *S. epidennidis*, are an important cause of infections associated with prosthetic devices and catheters (Vincent et al., *LAMA*, 1995, 27, 639). Although CNS display lower virulence than *S. aureus*, they have intrinsic low-level resistance to many antibiotics, including beta-lactams and glycopeptides. In addition, many of these bacteria produce slime (biofilm), making the treatment of prosthetic associated infections difficult and often necessitating the removal of the infected prosthesis or catheter (Costerton et al., *Ann Rev Microbiol.*, 1987, 41, 435).

*Streptococcus pneumoniae*, regarded as fully sensitive to penicillin for many years, has now acquired the genes for resistance to oral streptococci. The prevalence of these resistant strains is increasing rapidly worldwide, which will limit the therapeutic options in serious pneumococcal infections, including meningitis and pneumonia (Baquero, *Microb Drug Resist*, 1995, 1, 115). *Streptococcus pneumoniae* is the leading cause of infectious morbidity and mortality worldwide. In the U.S.A. pneumococcus is responsible for an estimated 50,000 cases of bacteremia, 3,000 cases of meningitis, 7 million cases of otitis media, and several hundred thousand cases of pneumonia. The overall yearly incidence of pneumococcal bacteremia is estimated to be 15 to 35 cases per 100,000. Current immunization of small children and the elderly have not addressed the high incidence of pneumococcal infection (Dowell, *Arch Intern Med*, 1999, 159, 2461; Communicable Disease Report (CDN), 1999, 10, 7; Baquero, *Microb Drug Resist*, 1995, 1, 115). Multi-drug resistant strains were isolated in the late 1970's and are now encountered worldwide (Baquero, *Microb Drug Resist*, 1995, 1, 115).

*Pseudomonas aeruginosa*, Pseudomonads species including *Burkholderia cepacia* and *Xanthomonas malthophilia*, Enterobacteriaceae including *E. coli*, Enterobacter species, and Klebsiella species, account for the majority of isolates in which resistance has emerged (Livermore, *Commun Dis Public Health*, 1998, 1, 74; Livermore, *J Antimicrob Chemother*, 1997, 39, 673; House of Lords Select Committee on Science and Technology. Resistance to antibiotics and other antimicrobial agents. London: HMSO, 1998). Cystitis, pneumonia, septicaemi, and postoperative sepsis are the most common types of infections. Most of the infections in intensive care unit (ICU) patients result from the patients' own endogenous flora and, in addition, up to 50% of ICU patients also acquire nosocomial infections, which are associated with a relatively high degree of morbidity and mortality (Richards et al., *Crit Care Med*, 1999, 5, 887; Chandrasekar et al., *Crit Care Med*, 1980, 15, 508; Northey et al., *Surg Gynaecol Obstet*, 1974, 139, 321). Microorganisms associated with these infections include Enterobacteriaceae 34%, *S. aureus* 30%, *P. aeruginosa* 29%, CNS 19% and fungi 17%.

Selective pressure caused by the use of broad-spectrum antibiotics has lead to multidrug resistance in Gram-negative bacteria. Each time a new drug is introduced, resistant subdlones appear, and currently the majority of isolates are resistant to at least one antimicrobial (Lepellier et al., *Clin Infect Dis*, 1999, 3, 548; Giwercman et al., *J Antimicrob Chemother*, 1990, 26, 247; Livermore, *Commun Dis Public Health*, 1998, 1, 74; Livermore, *J Antimicrob Chemother*, 1997, 39, 673).

The low-permeability cell envelope of *P. aeruginosa* differs from that of *E. coli*. Forty-six percent of *P. aerugi-* nosa isolates from Europe are resistant to one or more antibiotic. The ability of *P. aeruginosa* to produce slime (biofilm), and its rapid development of resistance during treatment, often leads to therapy failure. Multidrug resistant *P. aeruginosa* has also become endemic within some specialized ICUs, such as those treating bums patients and cystic fibrosis patients (Hsueh et al., *J Clin Microbiol*, 1998, 36, 1347; Bert et al., *J Antimicrob Chemother*, 1996, 37, 809).

Several international reports have highlighted the potential problems associated with the emergence of antimicrobial resistance in the bacteria mentioned above, and it is conceivable that patients with serious infections soon will no longer be treatable with currently available antimicrobials. The increasing incidence of resistant strains among clinical isolates of *S.aureus*, *S.epidermidis* (CNS), enterococci, *Streptococcus pneumoniae*, gram negative bacilli (coliforms) such as *E.coli*, *Klebsiella pneumoniae*, Pseudomonas species and Enterobacter species, make these bacteria major candidates for future PNA design.

In another aspect of the present invention, modified PNA molecules can be used to identify preferred targets for PNAs. Using the known or partially known genome of the target micro-organisms, e.g,. from genome sequencing or cDNA libraries, different PNA sequences can be constructed and linked to an effective anti-infective enhancing Peptide and thereafter tested for anti-infective activity. It may be advantageous to select PNA sequences that are shared by as many micro-organisms as possible, or shared by a distinct subset of micro-organisms, such as, for example, Gram-negative or Gram-positive bacteria, or shared by distinct micro-organisms, or specific for a single micro-organism.

In one embodiment of the invention, modified PNA molecules are used for the identification of PNA sequences that are effective in blocking essential functions in bacteria. Various PNA sequences are incorporated into modified PNA molecules, which are then tested for their ability to inhibit or reduce the growth of bacteria.

Another embodiment of the invention involves a method of identifing PNA sequences that are useful in inhibiting or reducing the growth of one or more bacteria. The method involves mixing modified PNA molecules of Formula I, which contain different PNA sequences, with one or more bacteria. The PNA sequences are selected so as to be complementary to at least one nucleotide sequence in each bacteria. PNA sequences that are effective in inhibiting or reducing the growth of one or more bacteria are identified.

The compounds of Formula I can be prepared in the form of pharmaceutically acceptable salts, especially acid-addition salts, including salts of organic acids and mineral acids. The term "pharmaceutically acceptable salts" refers to derivatives of the modified PNAs of Formula I and the modified oligonucleotides of Formula III wherein the parent molecule is modified by making acid or base salts thereof. The term "pharmaceutically acceptable" refers to those compounds, materials, compositions, and/or dosage forms which are, within the scope of reasonable medical judgment, suitable for use in contact with the tissues of human beings and animals without excessive toxicity, irritation, allergic response, or other problem or complication, commensurate with a reasonable benefit/risk ratio.

Examples of pharmaceutically acceptable salts include, but are not limited to, salts of organic acids such as formic acid, fumaric acid, acetic acid, propionic acid, glycolic acid, lactic acid, pyruvic acid, oxalic acid, succinic acid, malic acid, tartaric acid, citric acid, benzoic acid, salicylic acid, and the like. Suitable inorganic acid-addition salts include salts of hydrochloric, hydrobromic, sulphuric and phosphoric acids, and the like. Further examples of pharmaceutically acceptable inorganic or organic acid addition salts include the pharmaceutically acceptable salts listed in *Journal of Pharmaceutical Science*, 1977, 66, 2, which are known to the skilled artisan.

Pharmaceutically acceptable acid addition salts also include the hydrates that the compounds of the invention are able to form. The acid addition salts can be obtained as the direct products of compound synthesis. In the alternative, the free base can be dissolved in a suitable solvent containing the appropriate acid, and the salt isolated by evaporating the solvent or otherwise separating the salt and solvent. The compounds of this invention can form solvates with standard low molecular weight solvents using methods known to the skilled artisan.

In a further aspect of the present invention, the invention provides a composition for use in inhibiting growth or reproduction of infectious micro-organisms, comprising a modified PNA molecule according to the present invention. The term "composition" includes pharmaceutically acceptable compositions.

In one embodiment, the inhibition of the growth of micro-organisms is obtained through treatment with either the modified PNA molecule alone or in combination with antibiotics or other anti-infective agents. In another embodiment, the composition comprises two or more different modified PNA molecules. A second modified PNA molecule can be used to target the same bacteria as the first modified PNA molecule or to target different bacteria. In the latter situation, specific combinations of target bacteria may be selected for treatment. Alternatively, the target can be one or more genes that confer resistance to one or more antibiotics in one or more bacteria. In such a situation, the composition or the treatment further comprises the use of said antibiotic(s).

In another aspect, the present invention includes within its scope pharmaceutical compositions comprising, as an active ingredient, at least one of the compounds of the general Formula I, or a pharmaceutically acceptable salt thereof, together with a pharmaceutically acceptable carrier or diluent.

Pharmaceutical compositions of the present invention can be prepared by conventional techniques, e.g., as described in *Remington: The Science and Practice of Pharmacy*, 19$^{th}$ Ed., 1995. The compositions can appear in conventional forms, for example, capsules, tablets, aerosols, solutions, suspensions, or topical applications.

Typical compositions include a compound of Formula I or III, or a pharmaceutically acceptable acid addition salt thereof, associated with a pharmaceutically acceptable excipient, which may be a carrier or a diluent. The composition can be diluted by a carrier, or enclosed within a carrier that can be in the form of a capsule, sachet, paper or other container. In making the compositions, conventional techniques for the preparation of pharmaceutical compositions may be used. For example, the active compound can be mixed with a carrier, or diluted by a carrier, or enclosed within a carrier, which may be in the form of a ampoule, capsule, sachet, paper, or other container. When the carrier serves as a diluent, it may be a solid, semi-solid, or liquid material which acts as a vehicle, excipient, or medium for the active compound. The active compound can be adsorbed on a granular solid container, for example, in a sachet. Some examples of suitable carriers include water, salt solutions, alcohols, polyethylene glycols, polyhydroxyethoxylated castor oil, peanut oil, olive oil, gelatine, lactose, terra alba, sucrose, glucose, cyclodextrin, amylose, magnesium stearate, talc, gelatin, agar, pectin, acacia, stearic acid, or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include any sustained release material known in the art, such as glyceryl monostearate or glyceryl distearate, alone or mixed with a wax. The formulations may also include wetting agents, emulsifying and suspending agents, preserving agents, sweetening agents, thickeners or flavouring agents. The formulations of the invention may be formulated so as to provide quick, sustained, or delayed release of the active ingredient after administration to the patient by employing procedures well known in the art. The pharmaceutical compositions can be sterilized and mixed, if desired, with auxiliary agents, emulsifiers, salt for influencing osmotic pressure, buffers and/or coloring substances, and the like, that do not deleteriously react with the active compounds.

The route of administration can be any route that effectively transports the active compound to the appropriate or desired site of action, such as oral, nasal, rectal, pulmonary, transdermal or parenteral, e.g., depot, subcutaneous, intravenous, intraurethral, intramuscular, intranasal, ophthalmic solution, or an ointment, the parenteral or the oral route being preferred. If a solid carrier is used for oral administration, the preparation may be tabletted, placed in a hard gelatin capsule in powder or pellet form, or it can be in the form of a troche or lozenge. If a liquid carrier is used, the preparation may be in the form of a suspension or solution in water or a non-aqueous media, a syrup, emulsion, or soft gelatin capsules. Thickeners, flavorings, diluents, emulsifiers, dispersing aids or binders may be added.

For nasal administration, the preparation may contain a compound of formula I dissolved or suspended in a liquid carrier, in particular an aqueous carrier, for aerosol application. The carrier may contain additives such as solubilizing agents, e.g,. propylene glycol, surfactants, absorption enhancers, such as lecithin (phosphatidylcholine) or cyclodextrin, or preservatives such as parabenes. For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

In formulations for the treatment or prevention of infectious diseases in mammals, the amount of active, modified PNA molecule to be used is determined in accordance with the specific active drug, organism to be treated, and carrier of the organism. "Mammals" include, but are not limited to, humans, domestic animals, such as, for example, household pets, livestock and other farm animals, and non-domestic animals, such as wildlife.

Dosage forms suitable for oral, nasal, pulmonal or transdermal administration comprise from about 0.01 mg to about 500 mg, preferably from about 0.01 mg to about 100 mg of the compounds of Formula I or III admixed with a pharmaceutically acceptable carrier or diluent.

In a further aspect, the present invention relates to the use of one or more compounds of the general Formula I or III, or pharmaceutically acceptable salts thereof, for the preparation of a medicament for the treatment and/or prevention of infectious diseases.

The preceding description regarding pharmaceutically acceptable salts of modified PNA molecules and compositions comprising the modified PNA molecules of Formula I is not limited to the modified PNA molecules of Formula I and is equally applicable to the modified oligonucleotides of Formula III.

In yet another aspect of the present invention, the present invention concerns a method of treating or preventing infectious disease, comprising administering to a patient in need of treatment, or for prophylactic purposes, an effective amount of modified PNA or modified oligonucleotide according to the invention. Such a treatment may be in the form of administering a composition in accordance with the present invention. In particular, the treatment may be a combination of traditional antibiotic treatment and treatment with one or more modified PNA molecules that target genes responsible for resistance to antibiotics.

The phrase "effective amount" refers to that amount of modified PNA or modified oligonucleotide that is capable of abolishing, inhibiting, or retarding bacterial growth in mammals.

The term "antibiotic" refers to conventional antibiotics as ordinarily understood in the art, i.e., antimicrobial substances that have the ability to inhibit the growth of or to destroy microorganisms. Classes of antibiotics that can be used include, but are not limited to, tetracyclines (i.e. minocycline), rifamycins (i.e. rifampin), macrolides (i.e. erythromycin), penicillins (i.e. nafcillin), cephalosporins (i.e. cefazolin), other beta-lactam antibiotics (i.e. imipenem, aztreonam), aminoglycosides (i.e. gentamicin), chloramphenicol, sufonamides (i.e. sulfamethoxazole), glycopeptides (i.e. vancomycin), quinolones (i.e. ciprofloxacin), fusidic acid, trimethoprim, metronidazole, clindamycin, mupirocin, polyenes (i.e. amphotericin B), azoles (i.e. fluconazole) and beta-lactam inhibitors (i.e. sulbactam).

Examples of specific antibiotics that can be used include, but are not limited to, minocycline, rifampin, erythromycin, nafcillin, cefazolin, imipenem, aztreonam, gentamicin, sulfamethoxazole, vancomycin, ciprofloxacin, trimethoprim, metronidazole, clindamycin, teicoplanin, mupirocin, azithromycin, clarithromycin, ofloxacin, lomefloxacin, norfloxacin, nalidixic acid, sparfloxacin, pefloxacin, amifloxacin, enoxacin, fleroxacin, temafloxacin, tosufloxacin, clinafloxacin, sulbactam, clavulanic acid, amphotericin B, fluconazole, itraconazole, ketoconazole, nystatin, and the like. Other examples of antibiotics will readily suggest themselves to those of ordinary skill in the art.

The present invention also relates to a method for the disinfection of objects other than living beings, such as, for example, surgery tools, hospital inventory, dental tools, slaughterhouse inventory and tools, dairy inventory and tools, barber and beautician tools, and the like, which comprises contacting the stated objects with the modified PNA molecules and modified oligonucleotides.

As used herein, the term "contacting" is employed in the broadest possible sense to mean any method of juxtaposition. Thus, contacting the object to be disinfected with modified PNA molecules and modified oligonucleotides includes all manner of applying the modified PNA molecules and modified oligonucleotides to the object, including brushing, coating, spraying, mixing, dipping, and the like. It is also contemplated that contacting includes juxtaposition for longer or shorter periods of time.

EXAMPLES

The following examples are merely illustrative of the present invention and should not be considered as limiting of the scope of the invention in any way. The principle of the present invention is shown using *E. coli* as a test organism. However, as shown in Example 19, the advantageous effect applies in the same way to other bacteria. Additional objects, features, and advantages of the invention will be apparent from the following description of the presently preferred embodiments.

The following abbreviations related to reagents are used herein: (The monomers and the PNA sequences are stated in bold)

TABLE 1

| | |
|---|---|
| A monomer | N-(2-Boc-aminoethyl)-N-(N$^6$-(benzyloxycarbonyl)adenine-9-yl-acetyl)glycine |
| Boc | Tert butyloxycarbonyl |
| Boc-Lys(2-Cl-Z)-OH | N-α-Boc-N-ε-2-chlorobenzyloxycarbonyl-L-lysine |
| C monomer | N-(2-Boc-aminoethyl)-N-(N$^4$-(benzyloxycarbonyl)cytosine-1-yl-acetyl)glycine |
| DCM | Dichloromethane |
| DIEA | N,N-diisopropylethylamine |
| DMF | N,N-dimethylformamide |
| DMSO | Dimethyl sulfoxide |
| G monomer | N-(2-Boc-aminoethyl)-N-(N$^2$-(benzyloxycarbonyl)guanine-9-yl-acetyl)glycine |
| HATU | N-[(1-H-benzotriazole-1-yl)(dimethylamine)methylene]-N-methylmethanaminiumhexafluorophosphate N-oxide |
| HBTU | 2-(1-H-benzotriazole-1-yl)-1,1,3,3,-tetramethyluronium hexafluorophosphate |
| J monomer/nucleobase | N-(2-Boc-aminoethyl)-N-(N-2-(benzyloxycarbonyl) isocytosine-5-yl-acetyl)glycine |
| MBHA resin | p-methylbenzhydrylamine resin |
| NMP | N-methyl pyrrolidone |
| T monomer | N-(2-Boc-aminoethyl)-N-(thymine-1-yl-acetyl)glycine |
| TFA | Trifluoroacetic acid |
| TFSMA | Trifluoromethanesulphonic acid |
| Tris | 2-amino-2-(hydroxymethyl)-1,3-propanediol |

The following abbreviations relating to linking groups are used herein: (The linking groups as starting materials are indicated with capital letters whereas the linking groups in the finished peptide-PNA conjugate are indicated with small letters.)

TABLE 2

| Abbreviation | Linker (IUPAC) |
|---|---|
| SMCC | Succinimidyl 4-(N-maleimidomethyl)cyclohexane-1-carboxylate |
| LCSMCC | Succinimidyl 4-(N-maleimidomethyl)cyclohexane-1-carboxy-(6-amido-caproate) |
| MBS | Succinimidyl m-maleimido-benzoylate |
| EMCS | Succinimidyl N-ε-maleimido-caproylate |
| SMPH | Succinimidyl 6-(β-maleimido-propionamido)hexanoate |
| AMAS | Succinimidyl N-(α-maleimido acetate) |
| SMPB | Succinimidyl 4-(p-maleimidophenyl)butyrate |
| b.ALA | β-alanine |
| PHG | Phenylglycine |
| ACHC | 4-aminocyclohexanoic acid |
| b.CYPR | β-(cyclopropyl) alanine |
| AHA, AHEX | 6-amino-hexanoic acid |
| ADO, AEEA-OH | ((2-aminoethoxy)ethoxy)acetic acid or 8-amino-3,6-dioxaoctanoic acid |
| ADC | Amino dodecanoic acid |

General Procedures

The linking groups containing a succinimidyl group are shown in FIG. 5. All the linking groups are commercially available. Mixtures of solvents are indicated on a volume basis, i.e. 30/2/10 (v/v/v).

Preparative HPLC was performed on a DELTA PAK (Waters)(C18,15 µm, 300 Å, 300×7.8 mm, 3 ml/minute). A linear gradient from solvent A: 0.1% TFA in water to B: 0.1% TFA in acetonitrile was used. 0–2 minutes B 10%, 2–30 minutes 40% B, 30–35 minutes 100% B, 35–37 minutes 100% B, 37–38 minutes 10% B, 37–50 minutes 10% B.

Mass Spectrometry was performed on MALDI (Matrix Assisted Laser Desorption and Ionisation Time of Flight Mass Spectrometry) as HP MALDI-TOF# G2025A calibrated with peptide nucleic acids of the following weights: $MW_1$=1584.5 g/mol, $MW_2$=3179.0 g/mol and $MW_3$=4605.4 g/mol.

Example 1

Preparation of H-KFFKFFKFFK-ado-TTC AAA CAT AGT-$NH_2$ (SEQ ID NO:18)

The peptide-PNA-chimera H-KFFKFFKFFK-ado-TTC AAA CAT AGT-$NH_2$ (SEQ ID NO:18) was synthesized on 50 mg MBHA resin (loading 100 µmol/g) (novabiochem) in a 5 ml glass reactor with a D-2 glass filter. Deprotection was performed with 2×600 µL TFA/m-cresol 95/5 followed by washing with DCM, DMF, 5% DIEA in DCM and DMF. The coupling mixture was a 200 µl 0.26 M solution of monomer (Boc-PNA-T-monomer, Boc-PNA-A-monomer, Boc-PNA-G-monomer, Boc-PNA-C-monomer, Boc-AEEA-OH (ado) (PE Biosystems Inc.)) in NMP mixed with 200 µl 0.5 M DIEA in pyridine and activated for 1 minute with 200 µl 0.202 M HATU (PE-biosystems) in NMP. The coupling mixture for the peptide part was a 200 µl 0.52 M NMP solution of amino acid (Boc-Phe-OH and Boc-Lys(2-Cl-Z)-OH (novabiochem)) mixed with 200 µl 1 M DIEA in NMP and activated for 1 minute with 200 µl 0.45 M HBTU in NMP. After coupling, the resin was washed with DMF, DCM, and capped with 2×500 µl NMP/pyridine/acetic anhydride 60/35/5. Washing with DCM, DMF and DCM terminated the synthesis cycle. The oligomer was deprotected and cleaved from the resin using "low-high" TFMSA. The resin was rotated for 1 hour with 2 ml of TFA/dimethylsulfid/m-cresol/TFMSA 10/6/2/0.5. The solution was removed and the resin was washed with 1 ml of TFA and 1.5 ml of TFMSA/TFA/m-cresol 2/8/1 was added. The mixture was rotated for 1.5 hours and the filtrate was precipitated in 8 ml diethylether.

The precipitate was washed with 8 ml of diethylether. The crude oligomer was dissolved in water and purified by HPLC. Preparative HPLC was performed on a DELTA PAK (Waters) (C18,15 µm, 300 Å, 300×7.8 mm, 3 ml/minute) A linear gradient from solvent A: 0.1% TFA in water to B: 0.1% TFA in acetonitrile was used. 0–2 minutes B 10%, 2–30 minutes 40% B, 30–35 minutes 100% B, 35–37 minutes 100% B, 37–38 minutes 10% B, 37–50 minutes 10% B. MW calculated: 4791.9 g/mol; found on MALDI: 4791 g/mol.

Example 2

Maleimide Activation of PNA

PNA-oligomer ado-TTC AAA CAT AGT-$NH_2$ (SEQ ID NO:19) (purified by HPLC) (2 mg, 0.589 µmol, MW 3396.8) was dissolved and stirred for 15 minutes in NMP:DMSO 8:2 (2 ml). Succinimidyl 4-(N-maleimidomethyl)cyclohexane-1-carboxylate (SMCC) (PIERCE)(1.1 mg, 3.24 µmol, 5.5 eq.), dissolved in NMP (50 µl) and DIEA (34.7 µl, 198.7 µmol), was added to the solution. The reaction mixture was stirred for 2.5 hours. The product was precipitated in diethylether (10 mL) and the precipitate was washed with ether:NMP, 10:1(3×10 mL), and ether (3×10 mL). MW calculated: 3615.8 g/mol; found on MALDI: 3613.5 g/mol. The product was used without further purification.

Example 3

Conjugation of Peptide and Maleimide Activated PNA

A solution of peptide CKFFKFFKFFK (SEQ ID NO:20) (0.5 mg in 200 µl degassed Tris buffer 10 mM, pH 7.6 (329 nM)) was added to a solution of the above activated product (0.2 mg in 200 µl DMF:Water 1:1). The reaction mixture was stirred overnight. The target compound was purified by HPLC directly from the crude reaction mixture. Preparative HPLC was performed on a DELTA PAK (Waters) (C18,15 µm, 300 Å, 300×7.8 mm, 3 ml/minute) A linear gradient from solvent A: 0.1% TFA in water to B: 0.1% TFA in acetonitrile was used. 0–2 minutes B 10%, 2–30 minutes 40% B, 30–35 minutes 100% B, 35–37 minutes 100% B, 37–38 minutes 10% B, 37–50 minutes 10% B. MW calculated: 5133.0 g/mol; found on MALDI: 5133 g/mol.

Example 4

Preparation of H-LLKKLAKALKG-ahex-ado-CCATCTAATCCT-$NH_2$ (SEQ ID NO:21)

Preparation of H-LLKKLAKALKG-ahex-ado-CCATCTAATCCT-$NH_2$ (SEQ ID NO:21) was performed in accordance with example 1, except 6-aminohexanoic acid (ahex) and 8-amino-3,6-dioxaoctanoic acid (ado) were used as linkers.

Example 5

Preparation of H-KFFKFFKFF-ado-JTJTJJT-ado-ado-ado-TCCCTCTC-Lys-$NH_2$ (SEQ ID NO:22)

Preparation of H-KFFKFFKFF-ado-JTJTJJT-ado-ado-ado-TCCCTCTC-Lys-NH2 (SEQ ID NO:22) was performed in accordance with example 1, except PNA oligomer ado-JTJTJJT-ado-ado-ado-TCCCTCTC-Lys-$NH_2$ (SEQ ID NO:23) was used instead of ado-TTC AAA CAT AGT-$NH_2$ (SEQ ID NO:19). This PNA is a triplex forming bis-PNA in which C (cytosine) in the "Hoogsteen strand" is exchanged with the J nucleobases (a substitute for protonated C). This substitution assures efficient triplex formation at physiological pH (Egholm, et al., *Nucleic Acids Res.*, 1995, 23,217).

Example 6

Preparation of Peptide-PNA-chimeras

The following peptide-PNA-chimeras were prepared as described above.

TABLE 3

| | |
|---|---|
| 1 | H-KFFKFFKFFK-ado-CAT AGC TGT TTC-$NH_2$ (SEQ ID NO: 24) |
| 2 | H-FFKFFKFFK-ado-CAT AGC TGT TTC-$NH_2$ (SEQ ID NO: 25) |
| 3 | H-FKFFKFFK-ado-CAT AGC TGT TTC-$NH_2$ (SEQ ID NO: 26) |

TABLE 3-continued

4  H-KFFKFFK-ado-CAT AGC TGT TTC-NH$_2$
   (SEQ ID NO: 27)
5  H-FFKFFK-ado-CAT AGC TGT TTC-NH$_2$
   (SEQ ID NO: 28)
6  H-FKFFK-ado-CAT AGC TGT TTC-NH$_2$
   (SEQ ID NO: 29)
7  H-KFFK-ado-CAT AGC TGT TTC-NH$_2$
   (SEQ ID NO: 30)
8  H-FFK-ado-CAT AGC TGT TTC-NH$_2$
   (SEQ ID NO: 31)
9  H-FK-ado-CAT AGC TGT TTC-NH$_2$
   (SEQ ID NO: 32)
10 H-K-ado-CAT AGC TGT TTC-NH$_2$
   (SEQ ID NO: 33)
11 H-ado-CAT AGC TGT TTC-NH$_2$
   (SEQ ID NO: 34)
84 H-KFFKFFKFF-ado-CAT AGC TGT TTC-NH$_2$
   (SEQ ID NO: 35)
85 H-FFKFFKFF-ado-CAT AGC TGT TTC-NH$_2$
   (SEQ ID NO: 36)
86 H-FKFFKFF-ado-CAT AGC TGT TTC-NH$_2$
   (SEQ ID NO: 37)
87 H-KFFKFF-ado-CAT AGC TGT TTC-NH$_2$
   (SEQ ID NO: 38)
88 H-FFKFF-ado-CAT AGC TGT TTC-NH$_2$
   (SEQ ID NO: 39)
89 H-FKFF-ado-CAT AGC TGT TTC-NH$_2$
   (SEQ ID NO: 40)
90 H-KFF-ado-CAT AGC TGT TTC-NH$_2$
   (SEQ ID NO: 41)
91 H-FF-ado-CAT AGC TGT TTC-NH$_2$
   (SEQ ID NO: 42)
92 H-F-ado-CAT AGC TGT TTC-NH$_2$
   (SEQ ID NO: 43)
109 H-KFFKFFKFFK-ado-TTC AAA CAT AGT-NH$_2$
    (SEQ ID NO: 18)
136 H-KFFKFFKFFK-ado-TGA CTA GAT GAG-NH$_2$
    (SEQ ID NO: 44)
130 H-KFFKFFKFFK-ado-CCA TCT AAT CCT-NH$_2$
    (SEQ ID NO: 45)
140 H-KFF-ado-JTJTJJT-ado-ado-ado-TCC TCT C-Lys-NH$_2$
    (SEQ ID NO: 46)
141 H-FKFF-ado-JTJTJJT-ado-ado-ado-TCC TCT C-Lys-NH$_2$
    (SEQ ID NO: 47)
142 H-FFKFF-ado-JTJTJJT-ado-ado-ado-TCC TCT C-Lys-NH$_2$
    (SEQ ID NO: 48)
143 H-KFFKFF-ado-JTJTJJT-ado-ado-ado-TCC TCT C-Lys-NH$_2$
    (SEQ ID NO: 49)
144 H-FKFFKFF-ado-JTJTJJT-ado-ado-ado-TCC TCT C-Lys-NH$_2$
    (SEQ ID NO: 50)
145 H-FFKFFKFF-ado-JTJTJJT-ado-ado-ado-TCC TCT C-Lys-NH$_2$
    (SEQ ID NO: 51)
146 H-KFFKFFKFF-ado-JTJTJJT-ado-ado-ado-TCC TCT C-Lys-NH$_2$
    (SEQ ID NO: 52)
170 H-FFKFFKFFK-GGC-smcc-ado-TTC AAA CAT AGT-NH$_2$
    (SEQ ID NO: 53)
171 H-FFRFFRFFR-GGC-smcc-ado-TTC AAA CAT AGT-NH$_2$
    (SEQ ID NO: 54)
172 H-LLKLLKLLK-GGC-smcc-ado-TTC AAA CAT AGT-NH$_2$
    (SEQ ID NO: 55)
173 H-LLRLLRLLR-GGC-smcc-ado-TTC AAA CAT AGT-NH$_2$
    (SEQ ID NO: 56)
174 H-LLKKLAKALK-GC-smcc-ado-TTC AAA CAT AGT-NH$_2$
    (SEQ ID NO: 57)
175 H-KRRWPWWPWKK-C-smcc-ado-TTC AAA CAT AGT-NH$_2$
    (SEQ ID NO: 58)
176 H-KFKVKFVVKK-GC-smcc-ado-TTC AAA CAT AGT-NH$_2$
    (SEQ ID NO: 59)
177 H-LLKLLLKLLLK-C-smcc-ado-TTC AAA CAT AGT-NH$_2$
    (SEQ ID NO: 60)
178 H-FFKFFKFFK-GGC-smcc-ado-TTC AAA CAT AGT-NH$_2$
    (SEQ ID NO: 61)
179 H-KFFKFFKFFK-C-smcc-ado-TTC AAA CAT AGT-NH$_2$
    (SEQ ID NO: 62)
218 H-F-ado-CCA TCT AAT CCT-NH$_2$
    (SEQ ID NO: 63)
219 H-FF-ado-CCA TCT AAT CCT-NH$_2$
    (SEQ ID NO: 64)
220 H-KFF-ado-CCA TCT AAT CCT-NH$_2$
    (SEQ ID NO: 65)
221 H-FKFF-ado-CCA TCT AAT CCT-NH$_2$
    (SEQ ID NO: 66)
222 H-FFKFF-ado-CCA TCT AAT CCT-NH$_2$
    (SEQ ID NO: 67)
223 H-KFFKFF-ado-CCA TCT AAT CCT-NH$_2$
    (SEQ ID NO: 68)
224 H-FKFFKFF-ado-CCA TCT AAT CCT-NH$_2$
    (SEQ ID NO: 69)
225 H-FFKFFKFF-ado-CCA TCT AAT CCT-NH$_2$
    (SEQ ID NO: 70)
226 H-KFFKFFKFF-ado-CCA TCT AAT CCT-NH$_2$
    (SEQ ID NO: 71)
228 H-LLKKLAKALKG-ahex-ado-CCA TCT AAT CCT-NH$_2$
    (SEQ ID NO: 21)
229 H-LLKKLAKALKG-ado-ado-CCA TCT AAT CCT-NH$_2$
    (SEQ ID NO: 72)
230 H-KFFKFFKFFK-ado-ado-CCA TCT AAT CCT-NH$_2$
    (SEQ ID NO: 73)
231 H-KFFKFFKFFK-ahex-ado-CCA TCT AAT CCT-NH$_2$
    (SEQ ID NO: 74)
232 H$_2$N-KFFKFFKFFK-C-smcc-ado-CCA TCT AAT CCT-NH$_2$
    (SEQ ID NO: 75)
233 H$_2$N-LLKKLAKALK-GC-smcc-ado-CCA TCT AAT CCT-NH$_2$
    (SEQ ID NO: 76)
234 H$_2$N-KFFKFF-C-smcc-ado-CCA TCT AAT CCT-NH$_2$
    (SEQ ID NO: 77)
249 H-ado-TTC AAA CAT AGT-NH$_2$
    (SEQ ID NO: 78)
371 H$_2$N-KFFKVKFVVKK-C-smcc-ado-TTC AAA CAT AGT-NH$_2$
    (SEQ ID NO: 79)
381 H$_2$N-KFFKVKFVVKK-C-smcc-ado-TTG TGC CCC GTC-NH$_2$
    (SEQ ID NO: 80)

Example 7

Preparation of Peptide-PNA Chimeras

The peptide-PNA-chimeras listed in Table 4 were prepared as described in Example 1 using the linking groups as defined above.

TABLE 4

| PA no. | Sequence | MW |
| --- | --- | --- |
| 437 | H$_2$N-KKFKVKFVVKKC-achc-β.ala-TTCAAACATAGT-NH$_2$ (SEQ ID NO: 81) | 4808 |
| 432 | H-KFFKFFKFFK-achc-β.ala-TTCAAACATAGT-NH$_2$ (SEQ ID NO: 82) | 4848 |
| 418 | H$_2$N-KKFKVKFVVKKC-lcsmcc-ado-TTCAAACATAGT-NH$_2$ (SEQ ID NO: 83) | 5203 |
| 419 | H$_2$N-KKFKVKFVVKKC-mbs-ado-TTCAAACATAGT-NH$_2$ (SEQ ID NO: 84) | 5070 |
| 420 | H$_2$N-KKFKVKFVVKKC-emcs-ado-TTCAAACATAGT-NH$_2$ (SEQ ID NO: 85) | 5064 |
| 421 | H$_2$N-KKFKVKFVVKKC-smph-ado-TTCAAACATAGT-NH$_2$ (SEQ ID NO: 86) | 5135 |
| 422 | H$_2$N-KKFKVKFVVKKC-amas-ado-TTCAAACATAGT-NH$_2$ (SEQ ID NO: 87) | 5008 |

TABLE 4-continued

| PA no. | Sequence | MW |
|---|---|---|
| 423 | H$_2$N-KKFKVKFVVKKC-smpβ-ado-TTCAAACATAGT-NH$_2$ (SEQ ID NO: 88) | 5112 |
| 446 | H$_2$N-KKFKVKFVVKKC-lcsmcc-gly-TTCAAACATAGT-NH$_2$ (SEQ ID NO: 89) | 5109 |
| 447 | H$_2$N-KKFKVKFVVKKC-lcsmcc-β.ala-TTCAAACATAGT-NH$_2$ (SEQ ID NO: 90) | 5121 |
| 448 | H$_2$N-KKFKVKFVVKKC-lcsmcc-β.cypr-TTCAAACATAGT-NH$_2$ (SEQ ID NO: 91) | 5147 |
| 449 | H$_2$N-KKFKVKFVVKKC-lcsmcc-aha-TTCAAACATAGT-NH$_2$ (SEQ ID NO: 92) | 5163 |
| 450 | H$_2$N-KKFKVKFVVKKC-lcsmcc-adc-TTCAAACATAGT-NH$_2$ (SEQ ID NO: 93) | 5247 |

Example 8

Preparation of Peptide-DNA Chimeras

The peptide-PNA-chimeras listed in Table 5 were prepared as described in Example 1 using the linking groups as defined above.

TABLE 5

| PA no. | Mw | Sequence |
|---|---|---|
| S 201 | 4943,30 | H-KFFKFFKFFK-ado-ado-TTCAAACATAGT-NH$_2$ (SEQ ID NO: 94) |
| S 202 | 4841,40 | H-KFFKFFKFFK-ado-Gly-TTCAAACATAGT-NH$_2$ (SEQ ID NO: 95) |
| S 203 | 4881,40 | H-KFFKFFKFFK-ado-P-TTCAAACATAGT-NH$_2$ (SEQ ID NO: 96) |
| S 204 | 4897,50 | H-KFFKFFKFFK-ado-aha-TTCAAACATAGT-NH$_2$ (SEQ ID NO: 97) |
| S 205 | 4855,40 | H-KFFKFFKFFK-ado-β.ala-TTCAAACATAGT-NH$_2$ (SEQ ID NO: 98) |
| S 206 | 4909,50 | H-KFFKFFKFFK-ado-achc-TTCAAACATAGT-NH$_2$ (SEQ ID NO: 99) |
| S 207 | 4841,40 | H-KFFKFFKFFK-Gly-ado-TTCAAACATAGT-NH$_2$ (SEQ ID NO: 100) |
| S 208 | 4765,40 | H-KFFKFFKFFK-Gly-Gly-TTCAAACATAGT-NH$_2$ (SEQ ID NO: 101) |
| S 209 | 4805,50 | H-KFFKFFKFFK-Gly-P-TTCAAACATAGT-NH$_2$ (SEQ ID NO: 102) |
| S 210 | 4821,50 | H-KFFKFFKFFK-Gly-aha-TTCAAACATAGT-NH$_2$ (SEQ ID NO: 103) |
| S 211 | 4779,40 | H-KFFKFFKFFK-Gly-β.ala-TTCAAACATAGT-NH$_2$ (SEQ ID NO: 104) |
| S 212 | 4833,50 | H-KFFKFFKFFK-Gly-achc-TTCAAACATAGT-NH$_2$ (SEQ ID NO: 105) |
| S 213 | 4881,40 | H-KFFKFFKFFK-P-ado-TTCAAACATAGT-NH$_2$ (SEQ ID NO: 106) |
| S 214 | 4805,50 | H-KFFKFFKFFK-P-Gly-TTCAAACATAGT-NH$_2$ (SEQ ID NO: 107) |
| S 215 | 4845,50 | H-KFFKFFKFFK-P-P-TTCAAACATAGT-NH$_2$ (SEQ ID NO: 108) |
| S 216 | 4861,60 | H-KFFKFFKFFK-P-aha-TTCAAACATAGT-NH$_2$ (SEQ ID NO: 109) |
| S 217 | 4819,50 | H-KFFKFFKFFK-P-β.ala-TTCAAACATAGT-NH$_2$ (SEQ ID NO: 110) |
| S 218 | 4873,60 | H-KFFKFFKFFK-P-achc-TTCAAACATAGT-NH$_2$ (SEQ ID NO: 111) |
| S 219 | 4897,50 | H-KFFKFFKFFK-aha-ado-TTCAAACATAGT-NH$_2$ (SEQ ID NO: 112) |
| S 220 | 4821,50 | H-KFFKFFKFFK-aha-Gly-TTCAAACATAGT-NH$_2$ (SEQ ID NO: 113) |
| S 221 | 4861,60 | H-KFFKFFKFFK-aha-P-TTCAAACATAGT-NH$_2$ (SEQ ID NO: 114) |
| S 222 | 4877,60 | H-KFFKFFKFFK-aha-aha-TTCAAACATAGT-NH$_2$ (SEQ ID NO: 115) |
| S 223 | 4835,50 | H-KFFKFFKFFK-aha-β.ala-TTCAAACATAGT-NH$_2$ (SEQ ID NO: 116) |
| S 224 | 4889,70 | H-KFFKFFKFFK-aha-achc-TTCAAACATAGT-NH$_2$ (SEQ ID NO: 117) |
| S 225 | 4855,40 | H-KFFKFFKFFK-β.ala-ado-TTCAAACATAGT-NH$_2$ (SEQ ID NO: 118) |
| S 226 | 4779,40 | H-KFFKFFKFFK-β.ala-Gly-TTCAAACATAGT-NH$_2$ (SEQ ID NO: 119) |
| S 227 | 4819,50 | H-KFFKFFKFFK-β.ala-P-TTCAAACATAGT-NH$_2$ (SEQ ID NO: 120) |
| S 228 | 4835,50 | H-KFFKFFKFFK-β.ala-aha-TTCAAACATAGT-NH$_2$ (SEQ ID NO: 121) |
| S 229 | 4793,50 | H-KFFKFFKFFK-β.ala-β.ala-TTCAAACATAGT-NH$_2$ (SEQ ID NO: 122) |
| S 230 | 4847,60 | H-KFFKFFKFFK-β.ala-achc-TTCAAACATAGT-NH$_2$ (SEQ ID NO: 123) |
| S 231 | 4845,50 | H-KFFKFFKFFK-P-p-TTCAAACATAGT-NH$_2$ (SEQ ID NO: 124) |
| S 232 | 4845,50 | H-KFFKFFKFFK-P-P-TTCAAACATAGT-NH$_2$ (SEQ ID NO: 125) |
| S 233 | 4907,70 | H-KFFKFFKFFK-K-K-TTCAAACATAGT-NH$_2$ (SEQ ID NO: 126) |
| S 234 | 4945,70 | H-KFFKFFKFFK-F-F-TTCAAACATAGT-NH$_2$ (SEQ ID NO: 127) |
| S 235 | 4926,60 | H-KFFKFFKFFK-F-K-TTCAAACATAGT-NH$_2$ (SEQ ID NO: 128) |
| S 236 | 4926,60 | H-KFFKFFKFFK-K-F-TTCAAACATAGT-NH$_2$ (SEQ ID NO: 129) |
| S 237 | 4917,50 | H-KFFKFFKFFK-phg-ado-TTCAAACATAGT-NH$_2$ (SEQ ID NO: 130) |
| S 238 | 4841,50 | H-KFFKFFKFFK-phg-Gly-TTCAAACATAGT-NH$_2$ (SEQ ID NO: 131) |
| S 239 | 4881,60 | H-KFFKFFKFFK-phg-P-TTCAAACATAGT-NH$_2$ (SEQ ID NO: 132) |
| S 240 | 4897,60 | H-KFFKFFKFFK-phg-aha-TTCAAACATAGT-NH$_2$ (SEQ ID NO: 133) |
| S 241 | 4855,50 | H-KFFKFFKFFK-phg-β.ala-TTCAAACATAGT-NH$_2$ (SEQ ID NO: 134) |
| S 242 | 4909,60 | H-KFFKFFKFFK-phg-achc-TTCAAACATAGT-NH$_2$ (SEQ ID NO: 135) |
| S 243 | 4909,50 | H-KFFKFFKFFK-achc-ado-TTCAAACATAGT-NH$_2$ (SEQ ID NO: 136) |
| S 244 | 4833,50 | H-KFFKFFKFFK-achc-Gly-TTCAAACATAGT-NH$_2$ (SEQ ID NO: 137) |
| S 245 | 4873,60 | H-KFFKFFKFFK-achc-P-TTCAAACATAGT-NH$_2$ (SEQ ID NO: 138) |
| S 246 | 4889,60 | H-KFFKFFKFFK-achc-aha-TTCAAACATAGT-NH$_2$ (SEQ ID NO: 139) |
| S 247 | 4847,60 | H-KFFKFFKFFK-achc-β.ala-TTCAAACATAGT-NH$_2$ (SEQ ID NO: 140) |
| S 248 | 4901,70 | H-KFFKFFKFFK-achc-achc-TTCAAACATAGT-NH$_2$ (SEQ ID NO: 141) |

Example 9

Measurement of Bacterial Growth and Growth Inhibition

The ability of the compounds of the present invention to inhibit bacterial growth can be measured in many ways, which are clear to the skilled artisan. For the purpose of exemplifying the present invention, bacterial growth is measured by the use of a microdilution broth method according to NCCLS guidelines. The present invention is not limited to this means of detecting inhibition of bacterial growth. The following procedure illustrates one means for measuring bacterial growth and growth inhibition.

Bacterial strain: *E.coli* K12 MG1655

Media: 10% Mueller-Hinton broth, diluted with sterile water.

10% LB broth, diluted with sterile water.

100% Mueller-Hinton broth.

Trays: 96 well trays, Costar # 3474, Biotech Line AS, Copenhagen. (Extra low sorbent trays are used in order to prevent/minimize adhesion of PNA to tray surface).

A logphase culture of *E.coli* is diluted with fresh preheated medium and adjusted to a defined OD (here: Optical Density at 600 nm) in order to result in a final concentration of $5\times10^5$ and $5\times10^4$ bacteria/ml medium in each well, which contains 200 µl of bacterial culture. PNA is added to the bacterial culture to yield final concentrations ranging from 300 nM to 1000 nM. Trays are incubated at 37° C. by shaking in a robot analyzer, PowerWave$_x$, software KC$^4$ Kebo.Lab, Copenhagen, for 16 hours and optical densities are measured at 600 nM throughout the incubation in order to record growth curves. Wells containing bacterial culture without PNA are used as controls to ensure correct inoculum size and bacterial growth during the incubation. Cultures are tested in order to detect contamination.

The individual peptide-L-PNA constructs have molecular weights between approximately 4,200 and 5,000, depending upon the composition. All tests were therefore performed on a molar basis rather than on a weight/volume basis. Assuming an average MW of 4,500, a concentration of 500 nM equals 2.25 microgram/ml.

Growth Inhibitory Effect of PNA-constructs:

Bacterial growth is described by the lag phase, i.e., the period until (before) growth starts, the log phase, i.e., the period with maximal growth rate, the steady-state phase, and finally the death phase. These parameters are used to evaluate the inhibitory (Minimal Inhibitory Concentration, abbr. MIC) and bactericidal (Minimal Bactericidal Concentration, abbr. MBC) effect of PNA on bacterial growth by comparing growth curves with and without PNA. Total inhibition of bacterial growth is defined as: OD (16 hours)=OD (0 hours,) or no visible growth, according to NCCLS Guidelines.

In an initial screen modified PNA molecules are tested in the sensitive 10% medium assay. Positive results are then run in the 100% medium assay in order to verify the inhibitory effect in a more "real" environment (cf. the American guidelines (NCCLS)).

Example 10

Measurement of In Vivo Antibacterial Efficacy

In vivo antibacterial efficacy is established by testing a compound of the invention in the mouse peritonitis/sepsis model as described by N. Frimodt-Møller et al., 1999, Chap. 14, Handbook of Animal Models of Infection. A number of female NMRI mice are inoculated with $10^7$ cfu of *E. coli* ATCC 25922 intraperitoneally. At one hour post-infection the mice are treated once in groups with: 1) Gentamycin (38 mg/kg s.c.); 2) Ampicillin (550 mg/kg s.c.); 3) a compound of the invention (50–60 mg/kg i.v.); and 4) no treatment. Samples are drawn from blood and peritoneal fluid at 1, 2, 4, and 6 hours post infection, and cfu/ml are counted.

Example 11

Bacterial Growth Inhibition with PNAs Targeted Against Penicillin Binding Proteins (PBPs)

Description of a Primary Screen

The bacterial growth assay is designed to identify modified PNA molecules that inhibit or completely abolish bacterial growth. Growth inhibition results from antisense binding of PNA to mRNA of the targeted gene. The compound tested is present during the entire assay.

Components

The experimental bacterial strain used is *Escherichia coli* K12 MG1655 (*E. coli* Genentic Stock Center, Yale University, New Haven). The medium for growth is 10% sterile LB (Lurea Bertani) medium. *E. coli* test cells are pre-cultured in LB medium at 37° C. over night (over night culture). The screen is performed in 96-well microtiter plates at 37° C. with constant shaking. PNAs are dissolved in $H_2O$ as a 40× concentrated stock solution.

Assay Conditions

A fresh culture (test culture) is inoculated with an overnight culture and grown to mid-log-phase ($OD_{600}$ =0.1 corresponding to $10^7$ cells/ml) at 37° C. The test culture is diluted stepwise in the range $10^5$ to $10^1$ with 10% LB medium. 195 µl of diluted culture and 5 µl of a 40× concentrated PNA stock solution are added to each test well. 96-well microtiter plates are incubated in a microplate scanning spectrophotometer at 37° C. under constant shaking. $OD_{600}$ measurements are performed automatically every 3.19 minutes and recorded simultaneously.

Target Genes:

Penicillin Binding Proteins (PBPs)

PBPs act in the biosynthesis of murein (peptidoglycan), which is part of the envelope of Gram-positive and Gram-negative bacteria. PBPs are inhibited by the binding of penicillin, which acts as substrate analogue. Hydrolytic enzymes are activated by the accumulation of peptidoglycan intermediates and hydrolyze the peptidoglycan layer, causing lysis.

*E.coli* has 7–9 PBPs, including the high molecular weight PBPs: PBP1A and PBP1B, PBP2, and PBP3, and the low molecular weight PBPs: PBP 4–9. The high molecular weight PBPs are essential for growth, whereas the low molecular weight PBPs are not.

PNA Design No. 1

PNA26 has been designed according to the sequence of the mrcA (ponA) gene of *E. coli*, encoding PBP1A. The sequence of the mrcA gene (accession number X02164) was obtained from the EMBL sequence database (Heidelberg, Germany) Broome-Smith et al., *Eur J Biochem.*, 1985, 147, 437). The sequence of the mrcA gene is shown in FIG. 3.

The target region of PNA26 is the following:

sense 5' AATGGGAAATTTCCAGTGAAGTTCGTAAAG 3'(SEQ ID NO:142)

121---------+---------+---------+150 antisense 3' TTACCCTTTAAAGGTCACTTCAAG-CATTTC 5'(SEQ ID NO:143)

The coding and the non-coding (antisense) strands of the GTG start codon region are shown. The sequence of the GTG start codon region of the antisense strand and PNA26 are shown in the 5' to 3' orientation: antisense 5' CTTTAC-GAACTT<u>CAC</u>TGGAAATTTCCCATT 3'(SEQ ID NO:143) PNA26 H-KFFKFFKFFK-ado-<u>CAC</u>TGGAAATTT-Lys-NH$_2$ (SEQ ID NO:144) PNA26 is a 12mer PNA molecule (shown in bold) coupled to a 10 amino acid peptide.

Growth Assay with PNA26

The assay was performed as follows. Dilutions of the test culture corresponding to $10^5$, $10^4$, $10^3$, $10^2$ and $10^1$ cells/ml containing PNA26 at a final concentration of 1.5, 2.0, 2.5, 3.0 and 3.5 μM are incubated at 37° C. for 16 hours with constant shaking. Total inhibition of growth can be seen in cultures with $10^4$–$10^1$ cells/ml and a PNA concentration of at least 2.5 μM (Table 6).

PNA Design No. 2

PNA14 has been designed according to the sequence of the mrdA gene encoding PBP2. The sequence (accession number AE000168, bases 4051–5952) was obtained from the *E. coli* genome database at the NCBI (Genbank, National Centre for Biotechnology Information, USA). The sequence of the mrdA gene is shown in FIG. 4.

The target region of PNA14 is the following:

sense 5' GAGTAGAAAACGCAGCGGATGAAACTA-CAGAAC 3'(SEQ ID NO:145)

99---------+---------+---------+--- 131 antisense 3' CTCATCTTTTGCGTCGCCTACTTTGAT-GTCTTG 5'(SEQ ID NO:146) Both the coding (sense) and the non-coding (antisense) strand of the GTG start codon region are shown.

In the following sequence of the ATG start codon region of the antisense strand and PNA26 are shown in the 5' to 3' orientation: antisense 5' GTTCTGTAGTTT<u>CAT</u>CCGCTGCGTTTTCTACTC 3'(SEQ ID NO:146) PNA14 H-KFFKFFKFFK-ado-TTT<u>CAT</u>CCGCTG-Lys-NH$_2$ (SEQ ID NO:147) PNA14 is a 12mer PNA molecule (shown in bold) coupled to a 10 amino acid peptide.

Growth Assay with PNA14

The assay was performed as follows. Dilutions of the test culture corresponding to $10^5$, $10^4$, $10^3$, $10^2$ and $10^1$ cells/ml containing PNA14 at a final concentration of 1.3, 1.4 and 1.5 μM are incubated at 37° C. for 16 hours with constant shaking. Total inhibition of growth can be seen in cultures with $10^4$–$10^1$ cells/ml and a PNA concentration of at least 1.4 μM (Table 7).

Example 12

Bacterial Growth Inhibition with PNA Targeted Against the LacZ Gene

Peptides are truncated versions of the KFF-motif The basic peptide sequence is KFFKFFKFFK (SEQ ID NO:148) (PNA 1). PNA 2, 3, 4, 5, 6, 7, 8, 9, 10 and 11 all contain peptides which are truncated from the C-terminal end. PNA 84, 85, 86, 87, 88, 89, 90, 91 and 92 all contain peptides which are truncated from the N-terminal end. The PNA targeted against the LacZ-gene has been synthesized with and without an —NH$_2$ terminal lysine.

The assay was performed as follows. Dilutions of the test culture *E. coli* K12 corresponding to $5 \times 10^5$ and $5 \times 10^4$ cells/ml, containing truncated versions of the KFF-motif of the PNAs targeted against the LacZ gene, at final concentrations of 100, 300, 750 and 1500 nM, were incubated in M9 minimal broth with lactose as the sole carbon source (minimal media 9, Bie & Berntsen Cph) at 37° C. for 16 hours with constant shaking.

Total inhibition of growth was evident in cultures with $5 \times 10^4$–$10^5$ cells/ml and a PNA concentration of at least 300 nM (see Table 8). The results show that the basic KFF motif 10-mer, as well as truncated peptides thereof (4, 5, 6, and 9-mer), may be used to enhance the inhibitory effect of PNA.

TABLE 6

Bacterial growth inhibition with PNA 26; *E. coli* K12 in 10% Mueller-Hinton broth

| PNA | PNA conc. in wells nM 1500 | 2000 | 2500 | 3000–3500 |
|---|---|---|---|---|
| Bacterial concentration 26 | 1% 0.1% 0.1% 0.001% 0.0001% – – – – – | 1% 0.1% 0.1% 0.001% 0.0001% – – – – | 1% 0.1% 0.1% 0.001% 0.0001% (+) + + + + | 1% 0.1% 0.1% 0.001% 0.0001% + + + + + |

+: Total inhibition of bacterial growth
(+): Significantly extended lagphase, (more than five times)
–: Lagphase extended less than five times
nd: Not done

TABLE 7

Bacterial growth inhibition with PNA 14; *E. coli* K12 in 10% Mueller-Hinton broth

| PNA | PNA conc. in wells nM 1300 | 1400 | 1500 |
|---|---|---|---|
| Bacterial concentration 14 | 1% 0.1% 0.1% 0.001% 0.0001% – – – – – | 1% 0.1% 0.1% 0.001% 0.0001% (+) + + + + | 1% 0.1% 0.1% 0.001% 0.0001% + + + + + |

+: Total inhibition of bacterial growth
(+): Significantly extended lagphase, (more than five times)
–: Lagphase extended less than five times.
nd: Not done

TABLE 8

| | | | \multicolumn{8}{c}{PNA conc. in well (nM)} | | | | | | | |
|---|---|---|---|---|---|---|---|---|---|---|
| | No of bacteria/ml | | 100 | | 300 | | 750 | | 1500 | |
| PNA | Peptide | Lysine | $5 \times 10^5$ | $5 \times 10^4$ | $5 \times 10^5$ | $5 \times 10^4$ | $5 \times 10^5$ | $5 \times 10^4$ | $5 \times 10^5$ | $5 \times 10^4$ |
| 1 | 10-mer | + | − | − | Nd | − | − | (+) | − | Nd |
| 2 | 9-mer | + | − | − | Nd | − | − | − | − | Nd |
| 84 | 9-mer | − | − | − | Nd | − | − | + | − | Nd |
| 3 | 8-mer | + | − | − | Nd | − | − | − | − | Nd |
| 85 | 8-mer | − | − | − | Nd | − | − | − | − | Nd |
| 4 | 7-mer | + | − | − | Nd | − | − | − | − | Nd |
| 86 | 7-mer | − | − | − | Nd | − | − | − | − | Nd |
| 5 | 6-mer | + | − | − | Nd | − | − | − | − | Nd |
| 87 | 6-mer | − | − | − | Nd | + | − | + | − | Nd |
| 6 | 5-mer | + | − | − | Nd | − | − | (+) | − | Nd |
| 88 | 5-mer | − | − | − | Nd | − | − | − | − | Nd |
| 7 | 4-mer | + | − | − | Nd | − | − | (+) | − | Nd |
| 89 | 4-mer | − | − | − | Nd | − | − | − | − | Nd |
| 8 | 3-mer | + | − | − | Nd | − | − | − | − | Nd |
| 90 | 3-mer | − | − | − | Nd | − | − | − | − | Nd |
| 9 | 2-mer | + | − | − | Nd | − | − | − | − | Nd |
| 91 | 2-mer | − | − | − | Nd | − | − | − | − | Nd |
| 10 | 1-mer | + | − | − | Nd | − | − | − | − | Nd |
| 92 | 1-mer | − | − | − | Nd | − | − | − | − | Nd |
| 11 | 0-mer | + | − | − | Nd | − | − | − | − | Nd |

+: Total inhibition of bacterial growth.
+): Significantly extended lagphase, (more than five times)
−: Lagphase extended less than five times;
Nd: Not done Example 13

Bacterial Growth Inhibition with PNA Targeted Against the infA Gene of *E. coli* (Sequence as PNA 130)

PNA130 and PNAs 218–226, targeted against the infA-gene, were synthesized with peptides which were truncated versions of the KFF-motif.
Growth Assay with PNA130
The assay was performed as follows. Dilutions of the test culture *E. coli* K12, corresponding to $2 \times 10^4$ and $4 \times 10^4$ cells/ml, containing truncated versions of the KFF-motif in PNAs targeted against the infA-gene, at final concentrations of 200, 400, 600 800 and 1000 nM, were incubated in 10% Mueller-Hinton broth at 37° C. for 16 hours with constant shaking.

Total inhibition of growth was evident in cultures with $4 \times 10^4$–$2 \times 10^4$ cells/ml and a PNA concentration of at least 600 nM (Table 9). The results reveal that the basic KFF motif 10-mer, as well as truncated peptides thereof (6 and 9-mer), may be used to enhance the inhibitory effect of PNA.

TABLE 9

| PNA No of bacteria/ml | Peptide | \multicolumn{10}{c}{PNA conc. in wells (nM)} | | | | | | | | | |
|---|---|---|---|---|---|---|---|---|---|---|---|
| | | 200 | | 400 | | 600 | | 800 | | 1000 | |
| | | $4 \times 10^4$ | $2 \times 10^4$ | $4 \times 10^4$ | $2 \times 10^4$ | $4 \times 10^4$ | $2 \times 10^4$ | $4 \times 10^4$ | $2 \times 10^4$ | $4 \times 10^4$ | $2 \times 10^4$ |
| 218 | 1-mer | − | − | − | − | − | − | − | − | − | − |
| 219 | 2-mer | − | − | − | − | − | − | − | − | − | − |
| 220 | 3-mer | − | − | − | − | − | − | − | − | − | − |
| 221 | 4-mer | − | − | − | − | − | − | − | − | − | − |
| 222 | 5-mer | − | − | − | − | − | − | − | − | − | − |
| 223 | 6-mer | − | − | − | − | − | − | (+) | (+) | (+) | (+) |
| 224 | 7-mer | − | − | − | − | − | − | − | − | − | − |
| 225 | 8-mer | − | − | − | − | − | − | − | − | − | − |
| 226 | 9-mer | − | − | − | − | − | + | (+) | + | (+) | + |
| 130 | 10-mer | − | − | − | − | (+) | + | + | + | + | + |

+: Total inhibition of bacterial growth
(+): Significantly extended lagphase, (more than five times)
−: Lagphase extended less than five times
nd: Not done

Example 14

Bacterial Growth Inhibition with PNA Targeted Against the α-Sarcine Loop of Ribosomal RNA PNAs 140–146, targeted against the α-sarcine loop of ribosomal RNA, were synthesized with peptides which were truncated versions of the KFF-motif.

Growth Assay

The assay was performed as follows. Dilutions of the test culture *E. coli* K12, corresponding to $2 \times 10^4$ and $4 \times 10^4$ cells/ml, containing truncated versions of the KFF-motif in PNAs targeted against the a-sarcine loop of ribosomal RNA, at final concentrations of 200, 400, 600, 800 and 1000 nM, were incubated in 10% Mueller-Hinton broth at 37° C. for 16 hours with constant shaking.

Total inhibition of growth was evident in cultures with $5 \times 10^5$–$5 \times 10^4$ cells/ml and a PNA concentration of at least 200 nM (Table 10). The results demonstrate that the basic KFF motif 10-mer, as well as all truncated peptides thereof comprising at least 3 amino acids, may be used to enhance the inhibitory effect of PNA.

TABLE 10

| | | PNA conc. in wells (nM) | | | | | | | | | |
|---|---|---|---|---|---|---|---|---|---|---|---|
| | | 200 | | 400 | | 600 | | 800 | | 1000 | |
| PNA | Peptide | | | | | | | | | | |
| | Bacteria/ml | $5 \times 10^5$ | $5 \times 10^4$ | $5 \times 10^5$ | $5 \times 10^4$ | $5 \times 10^5$ | $5 \times 10^4$ | $5 \times 10^5$ | $5 \times 10^4$ | $5 \times 10^5$ | $5 \times 10^4$ |
| 140 | 3-mer | − | − | − | − | − | − | (+) | (+) | (+) | (+) |
| 141 | 4-mer | (+) | + | + | + | + | + | + | + | + | + |
| 142 | 5-mer | − | (+) | (+) | + | (+) | + | + | + | + | + |
| 143 | 6-mer | + | + | + | + | + | + | + | + | + | + |
| 144 | 7-mer | − | (+) | + | + | + | + | + | + | + | + |
| 145 | 8-mer | (+) | (+) | (+) | + | + | + | + | + | + | + |
| 146 | 9-mer | − | (+) | + | + | + | + | + | + | nd | nd |

+: Total inhibition of bacterial growth
(+): Significantly extended lagphase, (more than five times)
−: Lagphase extended less than five times
nd: Not done

Example 15

Bacterial Growth Inhibition with PNA Against the FtsZ Gene of *E. coli* K12

Growth Assay with PNA170–179 and 109

The assay was performed as follows. Dilutions of the test culture *E. coli* K12, corresponding to 700 and 350 cells/ml, containing variations of amphipathic 10, 11 and 12-mer structures with smcc-linker in PNAs targeted against the FtsZ-gene, at final concentrations of 200, 300, 400, 500, 600, 800 and 1000 nM, were incubated in 100% Mueller-Hinton broth at 37° C. for 16 hours with constant shaking.

Total inhibition of growth was evident in cultures with 350–700 cells/ml and a PNA concentration of at least 300 nM (Table 11). When comparing PNA109 with PNA 179, the smcc linker appears to add some advantages to the molecule. Further, sequence 174 shows promising results.

TABLE 11

| | No of | Conc. PNA construct | | | | | | | | | | | | |
|---|---|---|---|---|---|---|---|---|---|---|---|---|---|---|
| | bacteria/ml | 200 nM | | 300 nM | | 400 nM | | 500 nM | | 600 nM | | 800 nM | | 1000 nM | |
| PNA | Peptide | 700 | 350 | 700 | 350 | 700 | 350 | 700 | 350 | 700 | 350 | 700 | 350 | 700 | 350 |
| 170 | 12-mer | − | − | − | − | − | − | − | − | − | − | − | − | − | − |
| 171 | 12-mer | − | − | − | − | − | − | − | − | − | − | + | + | + | (+) |
| 172 | 12-mer | − | − | − | − | − | − | − | − | − | − | − | − | − | − |
| 173 | 12-mer | − | − | − | − | − | − | − | − | − | − | − | − | − | − |
| 174 | 12-mer | − | − | − | + | − | + | + | + | + | + | + | + | + | + |
| 175 | 12-mer | − | − | − | − | − | − | − | − | − | − | − | − | − | − |
| 176 | 12-mer | − | − | − | − | − | − | − | − | − | − | (+) | (+) | + | + |
| 177 | 12-mer | − | − | − | − | − | − | − | − | − | − | − | − | − | − |
| 178 | 12-mer | − | − | − | − | − | − | − | − | − | − | − | − | − | − |
| 179 | 11-mer | − | − | + | + | (+) | (+) | + | + | + | + | + | + | + | + |
| 109 | 10-mer | − | − | − | − | − | − | − | − | − | − | (+) | (+) | (+) | (+) |

+: Total inhibition of bacterial growth
(+): Significantly extended lagphase, (more than five times)
−: Lagphase extended less than five times;
nd: Not done

Example 16

Bacterial Growth Inhibition by PNAs, Which Contain Various Linkers and Peptides, Targeted against the Gene Encoding IF-1 of *E. coli*

For the 7 PNA's in this set-up, the sequence of the nucleobases is the same as the sequence in PNA 130, but the linking groups and the peptides vary.

TABLE 12

| PNA | Linker | Peptide |
|---|---|---|
| PNA228 | ahex-ado | G-KLAKALKKLL (SEQ ID NO: 149) |
| PNA229 | ado-ado | G-KLAKALKKLL (SEQ ID NO: 150) |
| PNA230 | ado-ado | KFFKFFKFF (SEQ ID NO: 151) |

TABLE 12-continued

| PNA | Linker | Peptide |
|---|---|---|
| PNA231 | ahex-ado | KFFKFFKFF (SEQ ID NO: 152) |
| PNA232 | smcc-ado | H-C-KFFKFFKFFK-NH$_2$ (SEQ ID NO: 153) |
| PNA233 | smcc-ado | H-CG-KLAKALKKLL-NH$_2$ (SEQ ID NO: 154) |
| PNA234 | smcc-ado | H-C-FFKFFK-NH$_2$ (SEQ ID NO: 155) |

The experimental set-up corresponds to the set-up as described in Example 15. As is evident from Table 13 and 14, the smcc-ado linker is the superior linker, demonstrating total inhibition of growth in cultures with $1.6 \times 10^3$–$8 \times 10^2$ cells/ml and a PNA concentration of at least 600 nM.

TABLE 13

| | PNA conc. in wells (nM) | | | | | | | | | | | | | | |
|---|---|---|---|---|---|---|---|---|---|---|---|---|---|---|---|
| | 200 | | | 400 | | | 600 | | | 800 | | | 1000 | | |
| | No of bacteria/ml based on counting of colonies on agar plates | | | | | | | | | | | | | | |
| PNA | 1590 | 795 | 159 | 1590 | 795 | 159 | 1590 | 795 | 159 | 1590 | 795 | 159 | 1590 | 795 | 159 |
| 228 | − | − | − | − | − | − | − | − | − | − | − | − | − | − | − |
| 229 | − | − | − | − | − | − | − | − | − | − | − | − | − | − | − |
| 230 | − | − | − | − | − | − | − | − | − | − | − | − | − | − | − |
| 231 | − | − | − | − | − | − | − | − | − | − | − | − | − | − | − |
| 232 | − | − | − | (+) | (+) | (+) | + | + | + | + | + | + | + | + | + |
| 233 | − | − | − | (+) | (+) | (+) | + | + | + | + | + | + | + | + | + |
| 234 | − | − | − | − | − | − | − | − | − | − | − | − | − | − | − |

Data from 100% MH
+: Total inhibition of bacterial growth
(+): Significantly extended lagphase, (more than five times)
−: Lagphase extended less than five times;
nd: Not done

TABLE 14

| | PNA conc. in wells (nM) | | | | | | | | | | | | | | |
|---|---|---|---|---|---|---|---|---|---|---|---|---|---|---|---|
| | 200 | | | 400 | | | 600 | | | 800 | | | 1000 | | |
| | No of bacteria/ml based on counting of colonies on agar plates | | | | | | | | | | | | | | |
| PNA | $10^5$ | $10^4$ | $10^3$ | $10^5$ | $10^4$ | $10^3$ | $10^5$ | $10^4$ | $10^3$ | $10^5$ | $10^4$ | $10^3$ | $10^5$ | $10^4$ | $10^3$ |
| 228 | − | − | − | − | − | − | − | − | − | − | − | (+) | − | (+) | + |
| 229 | − | − | − | − | − | − | − | − | − | (+) | (+) | − | (+) | + |
| 230 | − | − | − | (+) | (+) | + | + | + | + | + | + | + | + | + | + |
| 231 | − | − | − | − | (+) | (+) | (+) | + | + | + | + | + | + | + | + |
| 232 nd | | | | | | | | | | | | | | | |
| 233 nd | | | | | | | | | | | | | | | |
| 234 nd | | | | | | | | | | | | | | | |

Data from 10% MH
+: Total inhibition of bacterial growth;
(+): Significantly extended lagphase, (more than five times)
−: Lagphase extended less than five times;
nd: Not done

Example 17

Bacterial Growth Inhibition With 9 Mer Peptide

To test the effect of a Peptide without a PNA, peptide no. 2339, H-KFFKFFKFF-OH (SEQ ID NO:1), was added to *E. coli* K12 in 10% and 100% medium (Mueller-Hinton broth). Growth Assay of Peptide no. 2339

The assay was performed as follows. Dilutions of the test culture corresponding to $10^5$, $10^4$, and $10^3$ cells/ml containing peptide no. 2339 at a final concentration of 100 to 20,000 nM, were incubated at 37° C. for 16 hours with constant shaking. Total inhibition of growth was evident in cultures with $7.9 \times 10^3$ cells/ml and a peptide concentration of at least 20,000 nM, and minimal signs of growth inhibition were detected at concentrations from 5,000 nM (10% medium: Table 15; 100% medium: Table 16). The peptide was thus active alone, but only at very high concentrations which were above the range used for PNA growth assays.

TABLE 15

| Peptide | Peptide conc. in wells (nM) |||||||||||||||||
|---|---|---|---|---|---|---|---|---|---|---|---|---|---|---|---|---|---|
|  | No. of bacteria/ml based on counting of colonies on agar plates |||||||||||||||||
|  | 100 ||| 300 ||| 500 ||| 700 ||| 900 ||| 1100 |||
|  | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ |
| 2339 | − | − | − | − | − | − | − | − | − | − | − | − | − | − | − | − | − | − |
|  | 1300 ||| 1500 ||| 2500 ||| 5000 ||| 10000 ||| 15000 |||
|  | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ | $4.0 \times 10^4$ | $7.9 \times 10^3$ | $4.0 \times 10^3$ |
| 2339 | − | − | − | − | − | − | − | − | − | ((+)) | ((+)) | ((+)) | ((+)) | ((+)) | ((+)) | ((+)) | ((+)) | ((+)) |
|  | 20000 |||
|  | $4.0 \times 10^4$ | $7.9 \times 10^3$ | $4.0 \times 10^3$ |
| 2339 | ((+)) | + | + |

+: Total inhibition of bacterial growth
(+): Significantly extended lagphase, (more than five times)
((+)): Lagphase extended less than five times, but still with growth curve effect
−: Lagphase extended less than five times;
nd: Not done

TABLE 16

| Peptide | Peptide conc. in wells (nM) |||||||||||||||||
|---|---|---|---|---|---|---|---|---|---|---|---|---|---|---|---|---|---|
|  | No. of bacteria/ml based on counting of colonies on agar plates |||||||||||||||||
|  | 100 ||| 300 ||| 500 ||| 700 ||| 900 ||| 1100 |||
|  | 1600 | 160 | 16 | 1600 | 160 | 16 | 1600 | 160 | 16 | 1600 | 160 | 16 | 1600 | 160 | 16 | 1600 | 160 | 16 |
| 2339 | − | − | − | − | − | − | − | − | − | − | − | − | − | − | − | − | − | − |
|  | 1300 ||| 1500 ||| 2500 ||| 5000 ||| 10000 ||| 15000 |||
|  | 1600 | 160 | 16 | 1600 | 160 | 16 | 1600 | 160 | 16 | 1600 | 160 | 16 | 1600 | 160 | 16 | 1600 | 160 | 16 |
| 2339 | − | − | − | − | − | − | − | − | − | − | − | − | − | − | − | − | − | − |
|  | 20000 |||
|  | 1600 | 160 | 16 |
| 2339 | − | − | (+) |

+: Total inhibition of bacterial growth
(+): Significantly extended lagphase, (more than five times)
((+)): Lagphase extended less than five times, but still with growth curve effect
−: Lagphase extended less than five times;
nd: Not done

Example 18

Bacterial Growth Inhibition With 9 Mér peptide and non-sense PNA

Growth Assay of the Peptide no. 2339 Together With Non-sense PNA 136

The assay was performed as follows. Dilutions of the test culture corresponding to $10^5$, $10^4$, and $10^3$ cells/ml, containing PNA 136 alone or PNA 136 and peptide No. 2339 in equal amounts, at a final concentration of 400 to 1000 nM, were incubated at 37° C. for 16 hours with constant shaking. No growth inhibition was detected at any of the concentrations (Table 17). The nonsense PNA was thus not active in the chosen range.

TABLE 17

| | | PNA/Peptide conc. in wells (nM) | | | | | | | | | | |
|---|---|---|---|---|---|---|---|---|---|---|---|---|
| PNA | Peptide | Dilution factor for stock solution of bacteria with $OD_{600}$ = 0.1 | | | | | | | | | | |
| | | 400 | | | 500 | | | 600 | | | 700 | | |
| | | $F10^2$ | $F10^3$ | $F10^4$ | $F10^2$ | $F10^3$ | $F10^4$ | $F10^2$ | $F10^3$ | $F10^4$ | $F10^2$ | $F10^3$ | $F10^4$ |
| 136 | 2339 | – | – | – | – | – | – | – | – | – | – | – | – |
| | | – | – | – | – | – | – | – | – | – | – | – | – |
| | | 800 | | | 900 | | | 1000 | | | | | |
| | | $F10^2$ | $F10^3$ | $F10^4$ | $F10^2$ | $F10^3$ | $F10^4$ | $F10^2$ | $F10^3$ | $F10^4$ | | | |
| 136 | 2339 | – | – | – | – | – | – | – | – | – | | | |
| | | – | – | – | – | – | – | – | – | – | | | |

+: Total inhibition of bacterial growth
(+): Significantly extended lagphase, (more than five times)
((+)): Lagphase extended less than five times, but still with growth curve effect
–: Lagphase extended less than five times;
nd: Not done

Example 19

Bacterial Growth Inhibition With PNA (Without Peptide) Targeted Against the Gene Encoding FtsZ of E. coli and a Peptide E. coli K12 was grown in 100% Mueller-Hinton broth. PNA 249 is identical to PNA 109, without the peptide but still with the ado-linker. The Peptide of PNA 250 has the sequence: H-CG-KLAKALKKLL-NH$_2$ (SEQ ID NO:156). The peptide is also used for PNA 174. In the wells with both PNA and peptide there is equal amount PNA and peptide. As can be seen in Table 18, neither 249 nor 250 alone nor 249 and 250 together show any useful effect in the low concentration end. Only the peptide alone in concentrations above 2500 nM may show growth inhibition effect.

TABLE 18

| | | PNA conc. in wells (nM) | | | | | | | | | | | | | | |
|---|---|---|---|---|---|---|---|---|---|---|---|---|---|---|---|---|
| PNA | Peptide | No of bacteria/ml based on counting of colonies on agar plates | | | | | | | | | | | | | | |
| | | 250 | | | 500 | | | 750 | | | 1000 | | | 1500 | | |
| | | 170 | 17 | 8 | 170 | 17 | 8 | 170 | 17 | 8 | 170 | 17 | 8 | 170 | 17 | 8 |
| 249 | | – | – | – | – | – | – | – | – | – | – | – | – | – | – | – |
| | 250 | nd | nd | nd | – | – | – | nd | nd | nd | – | – | – | – | – | – |
| | | 2000 | | | 2500 | | | 5000 | | | 10000 | | | 20000 | | |
| | | 170 | 17 | 8 | 170 | 17 | 8 | 170 | 17 | 8 | 170 | 17 | 8 | 170 | 17 | 8 |
| 170 249 | 17 | 8 | 170 | 17 | 8 | 170 | 17 | 8 | 170 | 17 | 8 | 170 | 17 | 8 | | |
| 249 | | – | – | – | – | – | – | nd | nd | nd | nd | nd | nd | nd | nd | nd |
| | 250 | nd | nd | nd | – | – | – | (+) | (+) | + | + | + | + | + | + | + |
| | | 500 + 500 | | | 1000 + 1000 | | | 1500 + 1500 | | | 2500 + 2500 | | | | | |
| | | 170 | 17 | 8 | 170 | 17 | 8 | 170 | 17 | 8 | 170 | 17 | 8 | | | |
| 249 | 250 | – | – | – | – | – | – | – | – | – | – | – | – | | | |

+: Total inhibition of bacterial growth.
(+): Significantly extended lagphase, (more than five times)
–: Lagphase extended less than five times;
nd: Not done

Example 20

Bacterial Growth Inhibition With PNA Against the Gene Encoding IF-1 of E. coli E. coli K12 was grown in 10% Mueller-Hinton broth. Peptides are versions of the KFF-motif placed C- or N-terminal to the PNA. From Table 19 it can be seen that both orientation of the Peptide work. However, for specific combinations of PNA and Peptide, one of the orientations may be preferred.

Example 23

Gene Target Selection and Bacterial Growth Inhibition with PNA

Gene Target Selection in *E. faecalis/E. faecium*

The annotated *E. faecium* genome is, along with 250 other genomes, commercially available from Integrated Genomics, Chicago. Single annotated genes from both organisms are also available in Genbank.

TABLE 19

| | | | \multicolumn{15}{c}{PNA conc. in wells (nM) No of bacteria/ml based on counting of colonies on agar plates} |
|---|---|---|---|---|---|---|---|---|---|---|---|---|---|---|---|---|---|
| | | | \multicolumn{3}{c}{200} | \multicolumn{3}{c}{400} | \multicolumn{3}{c}{600} | \multicolumn{3}{c}{800} | \multicolumn{3}{c}{1000} |
| PNA | Peptide | Place | $5.2 \times 10^4$ | $2.6 \times 10^4$ | $5.2 \times 10^3$ | $5.2 \times 10^4$ | $2.6 \times 10^4$ | $5.2 \times 10^3$ | $5.2 \times 10^4$ | $2.6 \times 10^4$ | $5.2 \times 10^3$ | $5.2 \times 10^4$ | $2.6 \times 10^4$ | $5.2 \times 10^3$ | $5.2 \times 10^4$ | $2.6 \times 10^4$ | $5.2 \times 10^3$ |
| 130 | 10-me | N | − | − | − | − | (+) | (+) | (+) | + | + | + | + | + | + | + | + |
| 214 | 10-me | C | − | − | − | (+) | + | + | + | + | + | + | + | + | + | + | + |
| 215 | 9-me | C | − | − | − | (+) | + | + | (+) | + | + | + | + | + | + | + | + |
| 216 | 6-me | C | − | − | − | − | − | − | − | − | − | − | − | − | (+) | (+) |
| 223 | 6-me | N | − | − | − | − | − | − | − | − | − | − | − | − | − | − |
| 226 | 9-me | N | − | − | − | − | − | − | − | (+) | + | (+) | + | + | + | + | 52 |

+: Total inhibition of bacterial growth
(+): Significantly extended lagphase, (more than five times)
−: Lagphase extended less than five times
nd: Not done

Example 21

Inhibition of Bacterial Growth by PNA-peptide Specific for the Ribosomal α-Sarine Loop To demonstrate that the present invention may be used for the treatment of many micro-organisms, a selection of Gram-negative and Gram-positive bacteria were treated under the same assay conditions as used in example 14. The modified PNA molecule used was PNA 146.

| | Inhibition of growth |
|---|---|
| Gram-negative organisms | |
| *Escherichia coli* | + |
| *Klebsiella pneumonia* | + |
| *Pseudomonas aeruginosa* | + |
| *Salmonella typhimurium* | + |
| Gram-positive organisms | |
| *Staphylococcus aureus* | + |
| *Enterococcus faecium* | + |
| *Micrococcos luteus* | + |

Growth of the bacterial isolates was inhibited. Growth inhibition of different Gram-negative and Gram-positive organisms has thus been demonstrated under the same assay conditions as were used for the testing of *E. coli* K. 12.

Example 22

Preparation of Peptide-PNA-chimeras

The following peptide-PNA-chimera was prepared as described in Example 1: H$_2$N-SILAPLGTTLV-KKVATTLKKIFSKWKC-smcc-Ado-TTCTAACATTTA-NH$_2$ (SEQ ID NO:159).

In Vitro Experiments

The ability of PNA conjugates to inhibit bacterial growth is measured by the use of a microdilution broth method using 100% Mueller-Hinton broth, according to NCCLS Guidelines. A logphase culture of *E. faecium* is diluted with fresh, prewarmed medium and adjusted to a defined OD (here: Optical Density at 600 nm) to yield a final concentration of $1 \times 10^4$ bacteria/ml medium in each well, which contain 195 µl of bacterial culture. PNA is added to the bacterial culture to yield final concentrations ranging from 450 nM to 1500 nM. Trays (e.g. Costar #3474) are incubated at 35° C. by shaking in a robot analyzer (96 well microtiter format), PowerWave$_x$, software KC$^4$, Kebo.Lab, Copenhagen, for 16 hours and optical densities are measured at 600 nm during the incubation in order to record growth curves. All cultures are tested for the presence of contaminants.

MIC and MBC

Experiments were performed to evaluate the relationship between MIC's and MBC's (Minimal Bactericidal Concentration) of the PNA. The studies were performed using 3 strains of *Enterococcus faecium* obtained from American Type Culture Collection (ATCC). These strains served as initial indicators of possible interference from known in vivo-selected vancomycin resistance mechanisms. The table below summarizes the characteristics of the strains.

*E. facium* Strain: Description

8803: susceptible to vancomycin, ciprofloxacin, gentamycin, rifampin, teicoplanin ATCC 51550: multidrugresistant (ampicillin, ciprofloxacin, gentamycin, rifampin, teicoplanin, vancomycin ATCC 700221: Resistant to Vancomycin The experimental design is as follows. MIC's were detected as previously described. Trays were incubated at 35° C. for an additional 24 hours in order to analyze regrowth of inhibited bacteria (MBC's). The PNA conjugate from Example 22 was used as were bacterial strains 8803, 51550, and 700221. The PNA concentration in wells was 400, 800 and 1600 nM.

The Minimal Inhibitory Concentrations (MIC's) of the PNA conjugate were as follows:

| E. facium Strain | MIC µg/ml-(nM) | MBC (µg/ml)-nM |
|---|---|---|
| 8803 | ≦400 | ≦400 |
| ATCC 51550 | ≦400 | ≦400 |
| ATCC 700221 | ≦400 | ≦400 |
| Peptide control | | |
| The peptide conjugate of Example 22 | >5000 | >5000 |

Example 24

Preparation of Peptide-PNA-chimeras

The following peptide-PNA-chimera was prepared as described in Example 1: $H_2N$-KKFKVKFVVKKC-smcc-Ado-ACTTTGTCGCCC-$NH_2$ (SEQ ID NO:160).

Example 25

Gene Target Selection and Bacterial Growth Inhibition with PNA

The selection of potential gene targets and testing of resultant PNA constructs were performed with *Staphylococcus aureus* NCTC 8325, which was obtained from Prof. J. Iandolo, University of Oklahoma Health Sciences Center, Department of Microbiology and Immunology. The genome of *S. aureus* NCTC 8325 is currently being sequenced at the *S. aureus* Genome Sequencing Project at the University of Oklahoma's Advanced Center for Genome Technology (OU-ACGT). The genome is 2.80 Mb, and 2,581,379 bp have been sequenced. Annotated gene sequences are available from Genbank for a number of putative targets.

Target Selection Approach

The basic approach used was similar to that used in the previous example. Potential target genes were retrieved from the unfinished genome sequences of *S. aureus* at the OU-ACGT, as well as Genbank. The presence of homologous genes and target sequences in bacterial genomes were tested using the BLAST 2.0 programs at the NCBI (National Center for Biotechnology Information) www BLAST server. The antibacterial PNA conjugate prepared in Example 24 was used in the following experiments.

In Vitro Experiments

The ability of PNA to inhibit bacterial growth is measured by the use of a microdilution broth method using 100% Mueller-Hinton broth, according to NCCLS Guidelines. A logphase culture of *S aureus* is diluted with fresh, prewarmed medium and adjusted to a defined OD (here: Optical Density at 600 nm) in order to yield a final concentration of $1\times10^4$ bacteria/ml medium in each well, which contains 195 µl of bacterial culture. PNA is added to the wells in order to yield final concentrations of 450 nM to 1500 nM. Trays (e.g. Costar #3474) are incubated at 35° C. by shaking in a robot analyzer (96 well microtiter format), PowerWave$_x$, software $KC^4$ Kebo.Lab, Copenhagen, for 16 hours and optical densities are measured at 600 nm during the incubation in order to record growth curves. All cultures are tested for the presence of contaminants.

MIC and MBC:

Experiments were also performed to evaluate the relationship between MIC's (Minimal Inhibitory Concentration) and MBC's (Minimal Bactericidal Concentration) of the PNA's. The experiments were performed using the reference strain *Staphylococcus aureus* NCTC 8325 obtained from Prof. J. Iandolo, University of Oklahoma Health Sciences Center, Department of Microbiology and Immunology. Two vancomycin resistant isolates of *S.aureus* obtained from American Type Culture Collection were also used. These strains served as initial indicators of possible interference from known in vivo-selected vancomycin resistance mechanisms. The table below summarizes the characteristics of the strains.

| S. aureus Strain | Description | Vancomycin MIC (µg/ml) |
|---|---|---|
| 8325 | susceptible to methicillin, vancomycin | <0.5 |
| ATCC 700698 | intermediate vancomycin resistance Resistant to methicillin | 2 |
| ATCC 700698R | highly vancomycinresistant subclone of ATCC 700698 | 11 |

The experimental design is as follows. MIC's were detected as described above. Trays were incubated at 35° C. for an additional 24 hours in order to analyze regrowth of inhibited bacteria (MBC's). The PNA from Example 24 was used as were bacterial strains 8325, 700698, and 700698R. PNA concentrations in the wells were 400, 800 and 1600 nM. The Minimal Inhibitory Concentrations (MIC) were as follows:

| S. aureus Strain | MIC µg/ml-(nM) | MBC (µg/ml)-nM |
|---|---|---|
| 8325 | 800/1600 | 1600 |
| ATCC 700698 | 800/1600 | 1600 |
| ATCC 700698R | 800/1600 | ≧1600 |
| Peptide control | | |
| The peptide conjugate of Example 24 | >5000 | >5000 |

Example 26

Measurement of Antibacterial Effect In Vivo

A compound of the invention was tested for antibacterial effect in vivo according to the test described by N. Frimodt-Møller. Untreated animals developed fulminant clinical signs of infection. At all time points the compound of the invention suppressed the *E. coli* cfu/ml as compared to non-treated controls and was as efficient as the two positive controls.

All patents, patent publications, and literature references cited in this specification are hereby incorporated by reference in their entirety.

We claim:

1. A modified PNA molecule comprising:

H-KFFKFFKFFK-ado-TTC AAA CAT AGT-NH$_2$,
H-FFKFFKFFK-GGC-smcc-ado-TTC AAA CAT AGT-NH$_2$,
H-FFRFFRFFR-GGC-smcc-ado-TTC AAA CAT AGT-NH$_2$,
H-LLKLLKLLK-GGC-smcc-ado-TTC AAA CAT AGT-NH$_2$,
H-LLRLLRLLR-GGC-smcc-ado-TTC AAA CAT AGT-NH$_2$,
H-LLKKLAKALK-GC-smcc-ado-TTC AAA CAT AGT-NH$_2$,
H-KRRWPWWPWKK-C-smcc-ado-TTC AAA CAT AGT-NH$_2$,
H-KFKVKFVVKK-GC-smcc-ado-TTC AAA CAT AGT-NH$_2$,
H-LLKLLLKLLLK-C-smcc-ado-TTC AAA CAT AGT-NH$_2$,
H-FFKFFKFFK-GGC-smcc-ado-TTC AAA CAT AGT-NH$_2$,
H-KFFKFFKFFK-C-smcc-ado-TTC AAA CAT AGT-NH$_2$,
H-ado-TTC AAA CAT AGT-NH$_2$,
H$_2$N-KFFKVKFVVKK-C-smcc-ado-TTC AAA CAT AGT-NH$_2$,
H$_2$N-KKFKVKFVVKK-achc-β.ala-TTCAAACATAGT-NH$_2$,
H-KFFKFFKFFK-achc-β.ala-TCAAACATAGT-NH$_2$,
H$_2$N-KKFKVKFVVKKC-lcsmcc-ado-TTCAAACATAGT-NH$_2$,
H$_2$N-KKFKVKFVVKKC-mbs-ado-TTCAAACATAGT-NH$_2$,
H$_2$N-KKFKVKFVVKKC-emcs-ado-TTCAAACATAGT-NH$_2$,
H$_2$N-KKFKVKFVVKKC-smph-ado-TTCAAACATAGT-NH$_2$,
H$_2$N-KKFKVKFVVKKC-amas-ado-TTCAAACATAGT-NH$_2$,
H$_2$N-KKFKVKFVVKKC-smpb-ado-TTCAAACATAGT-NH$_2$,
H$_2$N-KKFKVKFVVKKC-lcsmcc-gly-TTCAAACATAGT-NH$_2$,
H$_2$N-KKFKVKFVVKKC-lcsmcc-β.ala-TTCAAACATAGT-NH$_2$,
H$_2$N-KKFKVKFVVKKC-lcsmcc-β.cypr-TTCAAACATAGT-NH$_2$,
H$_2$N-KKFKVKFVVKKC-lcsmcc-aha-TTCAAACATAGT-NH$_2$,
H$_2$N-KKFKVKFVVKKC-lcsmcc-ado-TTCAAACATAGT-NH$_2$,
H-KFFKFFKFFK-ado-ado-TTCAAACATAGT-NH$_2$,
H-KFFKFFKFFK-ado-Gly-TTCAAACATAGT-NH$_2$,
H-KFFKFFKFFK-ado-P-TTCAAACATAGT-NH$_2$,
H-KFFKFFKFFK-ado-aha-TTCAAACATAGT-NH$_2$,
H-KFFKFFKFFK-ado-β.ala-TTCAAACATAGT-NH$_2$,
H-KFFKFFKFFK-ado-achc-TTCAAACATAGT-NH$_2$,
H-KFFKFFKFFK-Gly-ado-TTCAAACATAGT-NH$_2$,
H-KFFKFFKFFK-Gly-Gly-TTCAAACATAGT-NH$_2$,
H-KFFKFFKFFK-Gly-P-TTCAAACATAGT-NH$_2$,
H-KFFKFFKFFK-Gly-aha-TTCAAACATAGT-NH$_2$,
H-KFFKFFKFFK-Gly-β.ala-TTCAAACATAGT-NH$_2$,
H-KFFKFFKFFK-Gly-achc-TTCAAACATAGT-NH$_2$,
H-KFFKFFKFFK-P-ado-TTCAAACATAGT-NH$_2$,
H-KFFKFFKFFK-P-Gly-TTCAAACATAGT-NH$_2$,
H-KFFKFFKFFK-P-P-TTCAAACATAGT-NH$_2$,
H-KFFKFFKFFK-P-aha-TTCAAACATAGT-NH$_2$,
H-KFFKFFKFFK-P-β.ala-TTCAAACATAGT-NH$_2$,
H-KFFKFFKFFK-P-achc-TTCAAACATAGT-NH$_2$,
H-KFFKFFKFFK-aha-ado-TTCAAACATAGT-NH$_2$,
H-KFFKFFKFFK-aha-Gly-TTCAAACATAGT-NH$_2$,
H-KFFKFFKFFK-aha-P-TTCAAACATAGT-NH$_2$,
H-KFFKFFKFFK-aha-aha-TTCAAACATAGT-NH$_2$,
H-KFFKFFKFFK-aha-β.ala-TTCAAACATAGT-NH$_2$,
H-KFFKFFKFFK-aha-achc-TTCAAACATAGT-NH$_2$,
H-KFFKFFKFFK-β.ala-ado-TTCAAACATAGT-NH$_2$,
H-KFFKFFKFFK-β.ala-Gly-TTCAAACATAGT-NH$_2$,
H-KFFKFFKFFK-β.ala-P-TTCAAACATAGT-NH$_2$,
H-KFFKFFKFFK-β.ala-aha-TTCAAACATAGT-NH$_2$,
H-KFFKFFKFFK-β.ala-β.ala-TTCAAACATAGT-NH$_2$,
H-KFFKFFKFFK-β.ala-achc-TTCAAACATAGT-NH$_2$,
H-KFFKFFKFFK-P-p-TTCAAACATAGT-NH$_2$,
H-KFFKFFKFFK-P-P-TTCAAACATAGT-NH$_2$,
H-KFFKFFKFFK-K-K-TTCAAACATAGT-NH$_2$,
H-KFFKFFKFFK-F-F-TTCAAACATAGT-NH$_2$,
H-KFFKFFKFFK-F-K-TTCAAACATAGT-NH$_2$,
H-KFFKFFKFFK-K-F-TTCAAACATAGT-NH$_2$,
H-KFFKFFKFFK-phg-ado-TTCAAACATAGT-NH$_2$,
H-KFFKFFKFFK-phg-Gly-TTCAAACATAGT-NH$_2$,
H-KFFKFFKFFK-phg-P-TTCAAACATAGT-NH$_2$,
H-KFFKFFKFFK-phg-aha-TTCAAACATAGT-NH$_2$,
H-KFFKFFKFFK-phg-β.ala-TTCAAACATAGT-NH$_2$,
H-KFFKFFKFFK-phg-achc-TTCAAACATAGT-NH$_2$,
H-KFFKFFKFFK-achc-ado-TTCAAACATAGT-NH$_2$,
H-KFFKFFKFFK-achc-Gly-TTCAAACATAGT-NH$_2$,
H-KFFKFFKFFK-achc-P-TTCAAACATAGT-NH$_2$,
H-KFFKFFKFFK-achc-aha-TTCAAACATAGT-NH$_2$,
H-KFFKFFKFFK-achc-β.ala-TTCAAACATAGT-NH$_2$ or
H-KFFKFFKFFK-achc-achc-TTCAAACATAGT-NH$_2$.

* * * * *